United States Patent
Koelle et al.

(10) Patent No.: US 6,413,518 B1
(45) Date of Patent: Jul. 2, 2002

(54) IMMUNOLOGICALLY SIGNIFICANT HERPES SIMPLEX VIRUS ANTIGENS AND METHODS FOR IDENTIFYING AND USING SAME

(75) Inventors: David M. Koelle, Seattle; Hongbo Chen, Shoreline; Lawrence Corey, Mercer Island; Nancy Ann Hosken; Patrick McGowan, both of Seattle; Steven P. Fling, Bainbridge Island; Christine M. Posavad, Seattle, all of WA (US)

(73) Assignees: University of Washington; Fred Hutchinson Cancer Research Center; Corixa Corporation, all of Seattle, WA (US)

( * ) Notice: Subject to any disclaimer, the term of this patent is extended or adjusted under 35 U.S.C. 154(b) by 0 days.

(21) Appl. No.: 09/672,595

(22) Filed: Sep. 28, 2000

Related U.S. Application Data

(60) Provisional application No. 60/157,181, filed on Sep. 30, 1999, provisional application No. 60/203,660, filed on May 12, 2000, and provisional application No. 60/218,104, filed on Jul. 13, 2000.

(51) Int. Cl.$^7$ .................. A16K 39/245; C12P 21/00; C12P 15/33; C12P 15/34; C12P 15/36

(52) U.S. Cl. ................. 424/186.1; 424/184.1; 424/231.1; 424/192.1; 435/69.1; 435/69.3; 435/91.1; 435/91.4; 536/23.5

(58) Field of Search .............. 424/231, 184.1, 424/186.1, 192.1; 435/69.1, 69.3, 91.1, 91.4; 536/23.5

(56) References Cited

U.S. PATENT DOCUMENTS

| | | | |
|---|---|---|---|
| 4,859,587 A | 8/1989 | Roizman | |
| 5,632,992 A | 5/1997 | Nesburn et al. | |
| 5,714,152 A | 2/1998 | Burke et al. | |

FOREIGN PATENT DOCUMENTS

| | | | |
|---|---|---|---|
| WO | WO 92/02251 | | 2/1992 |
| WO | WO 95/16779 | | 6/1995 |
| WO | WO 97/05265 | | 2/1997 |
| WO | WO-9820016 | * | 5/1999 |

OTHER PUBLICATIONS

M.A. Tigges et al.(1992) Human CD8$^+$ Herpes Simplex Virus–Specific Cytotoxic T–Lymphocyte Clones Recognize Diverse Virion Protein Antigens, *Journal of Virology*, 66(3):1622–1634.

C.M. Posavad et al. (1996) High Frequency of CD8$^+$ Cytotoxic T–Lymphoctye Precursors Specific for Herpes Simplex Viruses in Persons with Genital Herpes, *Journal of Virology* 70(11):8165–8168.

D.M. Koelle et al. (1998) Clearance of HSV–2 from Recurrent Genital Lesions Correlates with Infiltration of HSV–Specific Cytotoxic T Lymphoctyes, *The Journal of Clinical Investigation* 101(7):1500–1508.

D.M. Koelle et al. (1997) Preferrential Presentation of Herpes Simplex Virus T–Cell Antigen by HLA DQA1*0501/DQB1*0201 in Comparison to HLA DQA1*0201/DQB1*0201, *Human Immunlolgy* 53(2):195–205.

S. Reichstetter et al. (1999) MHC–Peptide Ligand Interactions Establish a Functional Threshold for Antigen–Specific T Cell Recognition, *Human Immunology* 60(7):608–618.

W.W. Kwok et al. (1991) Peptide Binding Affinity and pH Variation Establish Functional Thresholds for Activation of HLA–DQ–Restricted T Cell Recognition, *Human Immunology* 60(7):619–626.

D.M. Koelle et al. (1994) Direct Recovery of Herpes Simplex Virus (HSV)–Specific T Lymphocyte Clones from Recurrent Genital HSV–2 Lesions, *The Journal of Infectious Diseases* 169:956–61.

D.M. Koelle et al. (1994) Antigenic Specificities of Human CD$^+$ T–Cell Clones Recovered from Recurrent Genital Herpes Simples Virus Type 2 Lesions, *Journal of Virology* 68(5):2803–2810.

A. Dolan et al. (1998) The Genome Sequence of Herpes Simplex Virus Type 2, *Journal of Virology* 72(3):2010–2021.

G. Elliott and P. O'Hare (1997) Intercellular Trafficking and Protein Delivery by a Herpesvirus Structural Protein, *Cell* 88:223–233.

E. De Plaen et al. (1997) Cloning of Genes Coding for Antigens Recognized by Cytolytic T Lymphocytes, *Immunology Methods Manual* 692–718.

Tatman, J.D. et al., "Assembly of Herpes Simplex Virus Type 1 Using a Panel of Recombinant Baculoviruses," *Journal of General Virology*, (1994), 75, 1101–1113.

D.M. Koelle, (1995) The Roles of T Lymphocytes in Host Responses to Herpes Simplex Virus, Herpes, 2:83–88.

B. Roizman et al., "Herpes Simplex Viruses and Their Replication", In: Fundamental Virology, 2$^{nd}$ Edition, ed. Fields et al, Raven Press, New York, pp. 849–895.

(List continued on next page.)

Primary Examiner—Ali R. Salimi
Assistant Examiner—Bao Qun Li
(74) Attorney, Agent, or Firm—Gates & Cooper LLP

(57) ABSTRACT

The invention provides HSV antigens that are useful for the prevention and treatment of HSV infection. Disclosed herein are epitopes confirmed to be recognized by T-cells derived from herpetic lesions. T-cells having specificity for antigens of the invention have demonstrated cytotoxic activity against cells loaded with virally-encoded peptide epitopes, and in many cases, against cells infected with HSV. The identification of immunogenic antigens responsible for T-cell specificity provides improved anti-viral therapeutic and prophylactic strategies. Compositions containing antigens or polynucleotides encoding antigens of the invention provide effectively targeted vaccines for prevention and treatment of HSV infection.

12 Claims, 23 Drawing Sheets

OTHER PUBLICATIONS

Manickan, E. et al., *J. Virol*, (1995) 69(8) pp. 4711–4716.

O. Bjornberg, et al., "dUTPhase from Herpes Simplex Virus Type 1: Purification from infected Green Monkey Kidney (Vero) Cells and from an Overproducing *Escherichia coli* Strain", (1993), vol. 4, pp. 149–159. Protein Expression and Purification.

M. Williams et al., "Characterization of a Herpes Simplex Virus Type 2 Deoxyuridine Triphosphate Nucleotidohydrolase and Mapping of a Gene Conferring Type Specificity for the Enzyme", (1987) *Virology*, vol. 156, pp. 282–292.

M. Williams, "Deoxyuridine Triphosphate Nucleotidohydrolase Induced by Herpes Simplex Virus Type1", *Journal of Biological Chemistry* (1984) vol. 259(16), pp. 10080–10084.

D.M. Koelle et al., "Recognition of Herpes Simplex Virus Type 2 Tegument Proteins by CD4 T Cells Infiltrating Human Genital Herpes Lesions", *Journal of Virology*, (1998) vol. 72(9), pp. 7476–7483.

* cited by examiner

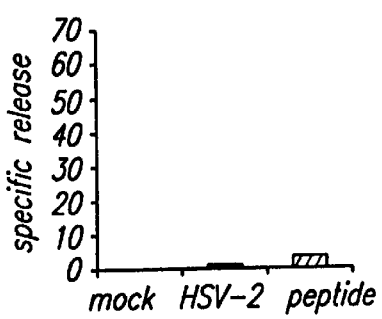
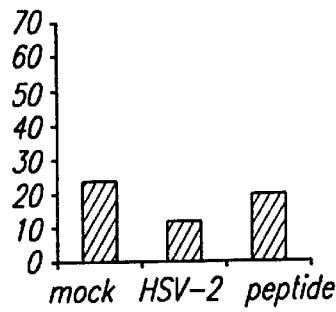
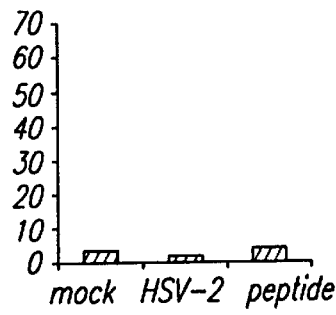
FIG. 10A  FIG. 10B  FIG. 10C
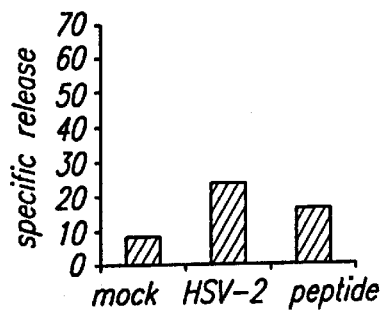
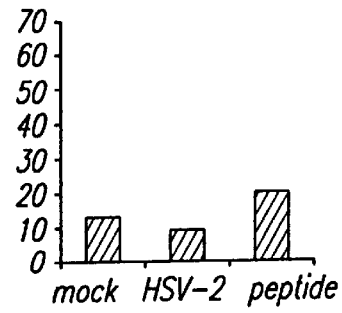
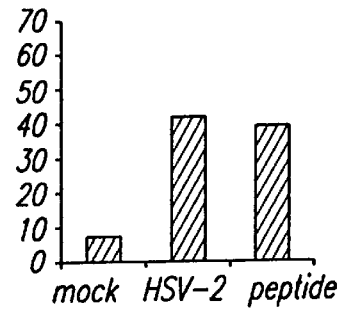
FIG. 10D  FIG. 10E  FIG. 10F
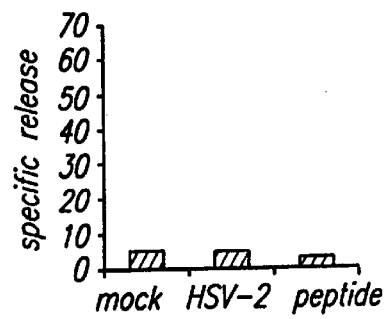
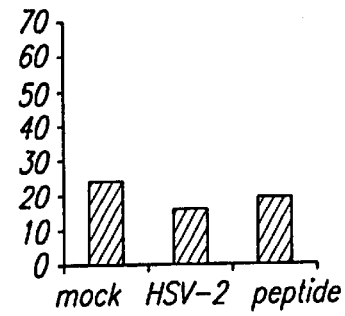
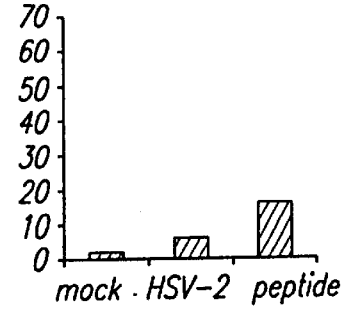
FIG. 10G  FIG. 10H  FIG. 10I

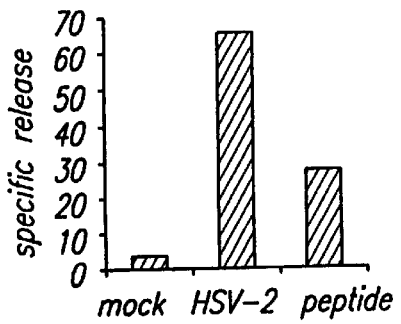 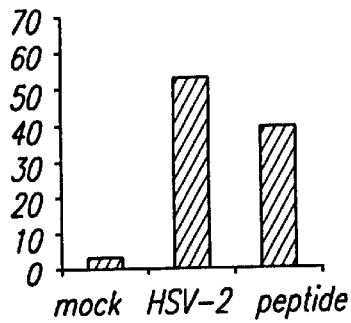 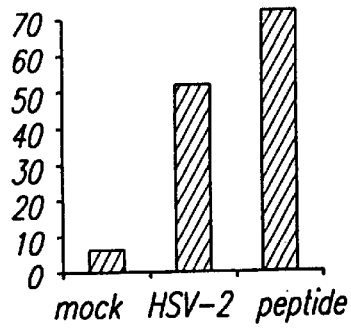
FIG. 10J    FIG. 10K    FIG. 10L
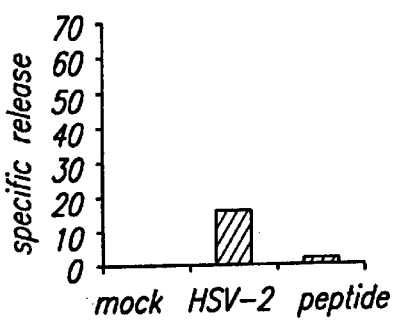 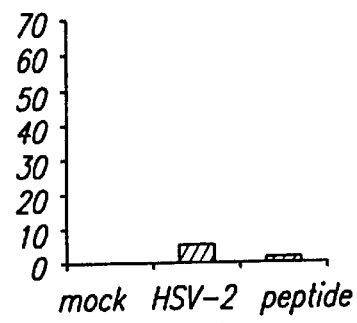 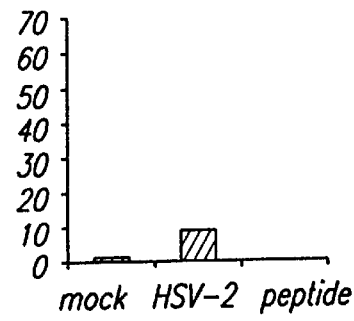
FIG. 10M    FIG. 10N    FIG. 10'O'

PCR primers used

| Number | Name | Sequence |
|---|---|---|
| 1790 | NJ67-MCS1 | 5'-CCTTACACAGTCCTGCTGAC-3' |
| 1791 | NJ68-MCS2 | 5'-GTTCCCGGGCCCTCACATTG-3' |
| 6421 | UL47/1652-1655 | 5'-GCCTGGCCCGACACG-3' |
| 6423 | UL47/1665-1652 | 5'-CGTGTCGGGCCAGGC-3' |

FIG. 17

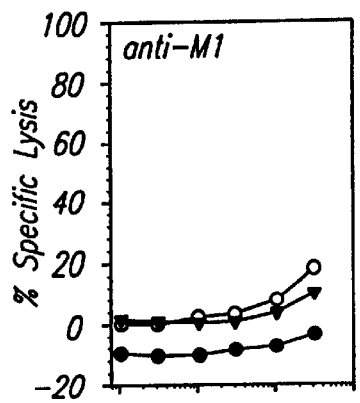
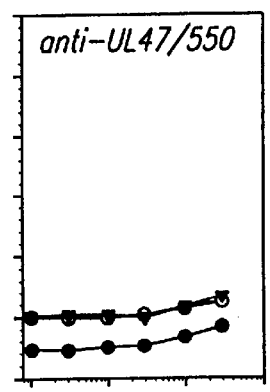
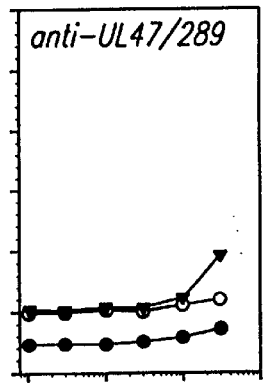
FIG. 20G        FIG. 20H        FIG. 20I
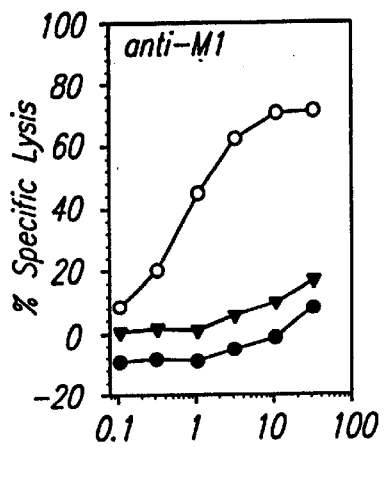
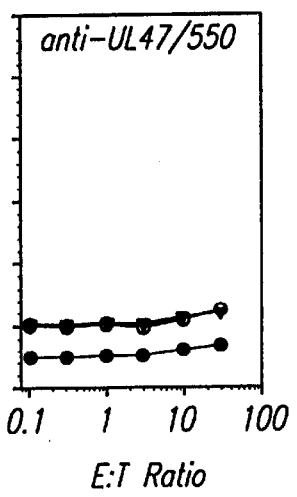
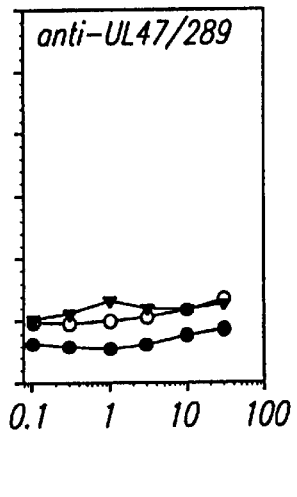
FIG. 20J        FIG. 20K        FIG. 20L

SEQUENCE LISTING

```
<160> NUMBER OF SEQ ID NOS: 20

<210> SEQ ID NO 1
<211> LENGTH: 10
<212> TYPE: PRT
<213> ORGANISM: Herpes Simplex Virus 2

<400> SEQUENCE: 1

Leu Gly Leu Ala Asp Thr Val Val Ala Cys
1               5                   10

<210> SEQ ID NO 2
<211> LENGTH: 10
<212> TYPE: PRT
<213> ORGANISM: Herpes Simplex Virus 2

<400> SEQUENCE: 2

Gly Leu Ala Asp Thr Val Val Ala Cys Val
1               5                   10

<210> SEQ ID NO 3
<211> LENGTH: 9
<212> TYPE: PRT
<213> ORGANISM: Herpes Simplex Virus 2

<400> SEQUENCE: 3

Gly Leu Ala Asp Thr Val Val Ala Cys
1               5

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
aaggtaccat gcgggtcacg gcaccccgaa                                      30

<210> SEQ ID NO 5
<211> LENGTH: 30
<212> TYPE: DNA
```

```
<213> ORGANISM: Artificial Sequence
<220> FEATURE:
<223> OTHER INFORMATION: Primer

<400> SEQUENCE: 5
ggtctagaag ttcgacactc tctgtgtagt                                         30

<210> SEQ ID NO 6
<211> LENGTH: 10
<212> TYPE: PRT
<213> ORGANISM: Herpes Simplex Virus 2

<400> SEQUENCE: 6

Ala Glu Arg Gln Gly Ser Pro Thr Thr Pro
 1               5                  10

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
ctaggatccc ctccggccac catgtcc                                            27

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
cgatctagac ctatgggcgt ggcgggc                                            27

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
cgaggatccg tctccgccat gcaacgccg                                          29

<210> SEQ ID NO 10
<211> LENGTH: 29
<212> TYPE: DNA
<213> ORGANISM: Artificial Sequence
<220> FEATURE:
<223> OTHER INFORMATION: Primer

<400> SEQUENCE: 10
cgctctagat tttaatggct ctggtgtcg                                          29

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
tgctctagag actcgatccc tgcgcgtcgg                                         30
```

<210> SEQ ID NO 12
<211> LENGTH: 31
<212> TYPE: DNA
<213> ORGANISM: Artificial Sequence
<220> FEATURE:
<223> OTHER INFORMATION: Primer

<400> SEQUENCE: 12
taaggtacct gaaccccggc ccggcacgag c                           31

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
tgctctagac caggcgtgcg gggcggcggg                             30

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ccttacacag tcctgctgac                                        20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gtttccgggc cctcacattg                                        20

<210> SEQ ID NO 16
<211> LENGTH: 14
<212> TYPE: DNA
<213> ORGANISM: Artificial Sequence
<220> FEATURE:
<223> OTHER INFORMATION: Primer

<400> SEQUENCE: 16
gcctggccga cacg                                              14

<210> SEQ ID NO 17
<211> LENGTH: 14
<212> TYPE: DNA
<213> ORGANISM: Artificial Sequence
<220> FEATURE:
<223> OTHER INFORMATION: Primer

<400> SEQUENCE: 17
cgtgtcggcc aggc                                              14

<210> SEQ ID NO 18
<211> LENGTH: 10
<212> TYPE: PRT
<213> ORGANISM: Herpes Simplex Virus 2

<400> SEQUENCE: 18

```
Arg Leu Leu Gly Leu Ala Asp Thr Val Val
 1               5                  10

<210> SEQ ID NO 19
<211> LENGTH: 14
<212> TYPE: PRT
<213> ORGANISM: Herpes Simplex Virus 2

<400> SEQUENCE: 19

Ala Glu Arg Gln Gly Ser Pro Thr Pro Ala Asp Ala Gln Gly
 1               5                  10

<210> SEQ ID NO 20
<211> LENGTH: 10
<212> TYPE: PRT
<213> ORGANISM: Herpes Simplex Virus 2

<400> SEQUENCE: 20

Phe Leu Val Asp Ala Ile Val Arg Val Ala
 1               5                  10
```

IMMUNOLOGICALLY SIGNIFICANT HERPES SIMPLEX VIRUS ANTIGENS AND METHODS FOR IDENTIFYING AND USING SAME

This application claims benefit of U.S. provisional patent applications No. 60/157,181, filed Sep. 30, 1999, Ser. No. 60/203,660, filed May 12, 2000, and Ser. No. 60/218,104, filed Jul. 13, 2000, the entire contents of each of which are incorporated herein by reference. Throughout this application various publications are referenced. The disclosures of these publications in their entireties are hereby incorporated by reference into this application in order to describe more fully the state of the art to which this invention pertains.

The invention disclosed herein was made with government support under Grant Nos. AI34616, AI30731 and CA70017, awarded by the National Institutes of Health. The government has certain rights in this invention.

TECHNICAL FIELD OF THE INVENTION

The invention relates to molecules, compositions and methods that can be used for the treatment and prevention of HSV infection. More particularly, the invention identifies epitopes of HSV proteins that can be used for the development of methods, molecules and compositions having the antigenic specificity of HSV-specific T cells, and in particular, of CD8+ T cells.

BACKGROUND OF THE INVENTION

Cellular immune responses are required to limit the severity of recurrent HSV infection in humans. Initial genital HSV-2 infections are prolonged and severe, while recurrences are less severe and more frequently asymptomatic. Resolution of primary HSV-2 infection is associated with infiltration of antigen-specific T cells, including CD8+ cytotoxic T lymphocytes (CTLs). Serial lesion biopsy studies of recurrent HSV-2 infection in humans has shown a shift to CD8+ predominance as lesions mature and correlation of local CTL activity with virus clearance (Koelle, D M et al., J. Clin. Invest. 1998, 101:1500–1508; Cunningham, A L et al., J. Clin. Invest. 1985, 75:226–233). Thus, HSV antigens recognized by CD8+ CTL can be used for novel therapies and vaccines.

The complete DNA sequence of herpes simplex virus (HSV) is approximately 150 kb and encodes about 85 known genes, each of which encodes a protein in the range of 50–1000 amino acids in length. Unknown are the immunogenic epitopes within these proteins, each epitope approximately 9–12 amino acids in length, that are capable of eliciting an effective T cell immune response to viral infection.

There remains a need to identify specific epitopes capable of eliciting an effective immune response to HSV infection. Such information can lead to the identification of more effective immunogenic antigens useful for the prevention and treatment of HSV infection.

SUMMARY OF THE INVENTION

The invention provides HSV antigens, polypeptides comprising HSV antigens, polynucleotides encoding the polypeptides, vectors, and recombinant viruses containing the polynucleotides, antigen-presenting cells (APCs) presenting the polypeptides, immune cells directed against HSV, and pharmaceutical compositions. The pharmaceutical compositions can be used both prophylactically and therapeutically. The antigens of the invention are recognized by T cells recovered from herpetic lesions. The invention additionally provides methods, including methods for preventing and treating HSV infection, for killing HSV-infected cells, for inhibiting viral replication, for enhancing secretion of antiviral and/or immunomodulatory lymphokines, and for enhancing production of HSV-specific antibody. For preventing and treating HSV infection, for enhancing secretion of antiviral and/or immunomodulatory lymphokines, for enhancing production of HSV-specific antibody, and generally for stimulating and/or augmenting HSV-specific immunity, the method comprises administering to a subject a polypeptide, polynucleotide, recombinant virus, APC, immune cell or composition of the invention. The methods for killing HSV-infected cells and for inhibiting viral replication comprise contacting an HSV-infected cell with an immune cell of the invention. The immune cell of the invention is one that has been stimulated by an antigen of the invention or by an APC that presents an antigen of the invention. A method for producing such immune cells is also provided by the invention. The method comprises contacting an immune cell with an APC, preferably a dendritic cell, that has been modified to present an antigen of the invention. In a preferred embodiment, the immune cell is a T cell such as a CD4+ or CD8+ T cell.

In one embodiment, the invention provides a composition comprising an HSV polypeptide. The polypeptide comprises an ICP0 or $U_L47$ protein or a fragment thereof. In one embodiment, the fragment comprises amino acids 92–101 of ICP0 or a substitutional variant thereof. In other embodiments, the fragment comprises amino acids 289–298, 548–557, 550–559, 551–559 and/or 551–561 of $U_L47$ or a substitutional variant thereof. Also provided is an isolated polynucleotide that encodes a polypeptide of the invention, and a composition comprising the polynucleotide. The invention additionally provides a recombinant virus genetically modified to express a polynucleotide of the invention, and a composition comprising the recombinant virus. In preferred embodiments, the virus is a vaccinia virus, canary pox virus, HSV, lentivirus, retrovirus or adenovirus. A composition of the invention can be a pharmaceutical composition. The composition can optionally comprise a pharmaceutically acceptable carrier and/or an adjuvant.

The invention additionally provides a method of identifying an immunogenic epitope of an infectious organism, such as a virus, bacterium or parasite. Preferably, the infectious organism is a virus, such as HSV. In one embodiment, the method comprises preparing a collection of random fragments of the organismal genome. The fragments can be prepared using any of a variety of standard methods, including, but not limited to, digestion with restriction enzymes and mechanical fragmentation, such as by controlled sonication (Mougneau E et al., Science 1995, 268:563–66). In a preferred embodiment, the organism is HSV-2 and the fragments of viral genome are prepared by digestion with Sau3A I. Examples of other restriction enzymes that can be used include, but are not limited to, Apa I, Sma I, and Alu I. The fragments of genomic DNA are then ligated into a vector, preferably by using a partial fill-in reaction. A preferred vector is a member of the pcDNA3.1 (+) his series. The fragments are then expressed using conventional techniques. Preferably, the expression is performed using a Cos-7 transfection method (De Plaen E et al. In: Lefkowits I, ed. Immunology Methods Manual, v. 2. New York: Academic Press, 1997:691–718). The Cos-7 cells can be co-transfected with an appropriate HLA molecule capable of presenting the target antigen.

The ability of the expressed polypeptide to elicit a cellular immune response is then assayed. Ability to elicit a cellular immune response is indicative of the presence of an immunogenic epitope. Assays that can be used to detect ability to elicit a cellular immune response include, but are not limited to, cytotoxicity assays and lymphokine secretion assays. In one embodiment, the assay is an interferon-gamma assay.

In a preferred embodiment, the invention provides a method for identifying HSV epitopes immunogenic for CD8+ T cells. The method comprises obtaining CD8+ T cells from an HSV lesion, and assaying the obtained T cells to identify T cells having ability to recognize HSV-infected cells. The method further comprises obtaining and fragmenting a nucleic acid preparation from HSV, expressing one or more fragments of the obtained nucleic acid, and assaying the expressed fragments for antigenic reactivity with the identified HSV-specific T cells. An expressed fragment having reactivity with the HSV-specific T cells is identified as encoding an HSV epitope immunogenic for CD8+ T cells.

The above steps can be repeated with sub fragments of the genome fragments. The method can further comprise sequencing a fragment of the genome. In one embodiment, the assaying of T cells comprises performing a cytotoxicity assay or an interferon-gamma assay. The assaying can be performed with an immune cell derived from a subject that has been exposed to the infectious organism. In preferred embodiments, the cell is derived from a site of active infection, such as skin or cervix, or from blood of an infected subject.

The invention further provides immunogenic epitopes identified by the method of the invention, polypeptides comprising the epitopes, and polynucleotides encoding the polypeptides. Suitable infectious organisms include bacteria, parasites and viruses. Examples of viruses include DNA and RNA viruses, both double-stranded and single-stranded. The method of the invention provides a strategy for combating a variety of infectious organisms, including those that exhibit significant variability, as knowledge of the organism's nucleic acid sequence is not required.

BRIEF DESCRIPTION OF THE FIGURES

FIGS. 10A–O show the presence of $U_L47$-specific CTL in peripheral blood lymphocytes.

FIG. 10A shows specific release for subject 1874 elicited by $U_L47$ 289–298.

FIG. 10B shows specific release for subject 1874 elicited by $U_L47$ 551–559.

FIG. 10C shows specific release for subject 1874 elicited by gB2 443–451.

FIG. 10D shows specific release for subject 7282 elicited by $U_L47$ 289–298.

FIG. 10E shows specific release for subject 7282 elicited by $U_L47$ 551–559.

FIG. 10F shows specific release for subject 7282 elicited by gB2 443–451.

FIG. 10G shows specific release for subject 9107 elicited by $U_L47$ 289–298.

FIG. 10H shows specific release for subject 9107 elicited by $U_L47$ 551–559.

FIG. 10I shows specific release for subject 9107 elicited by gB2 443–451.

FIG. 10J shows specific release for subject 9383 elicited by $U_L47$ 289–298.

FIG. 10K shows specific release for subject 9383 elicited by $U_L47$ 551–559.

FIG. 10L shows specific release for subject 9383 elicited by gB2 443–451.

FIG. 10M shows specific release for subject 9410 elicited by $U_L47$ 289–298.

FIG. 10N shows specific release for subject 9410 elicited by $U_L47$ 551–559.

FIG. 10O shows specific release for subject 9410 elicited by gB2 443–451.

549–557 (open circles); 550–558 (solid triangles); 551–559 (open triangles); 552–560 (squares).

Figure 11A:
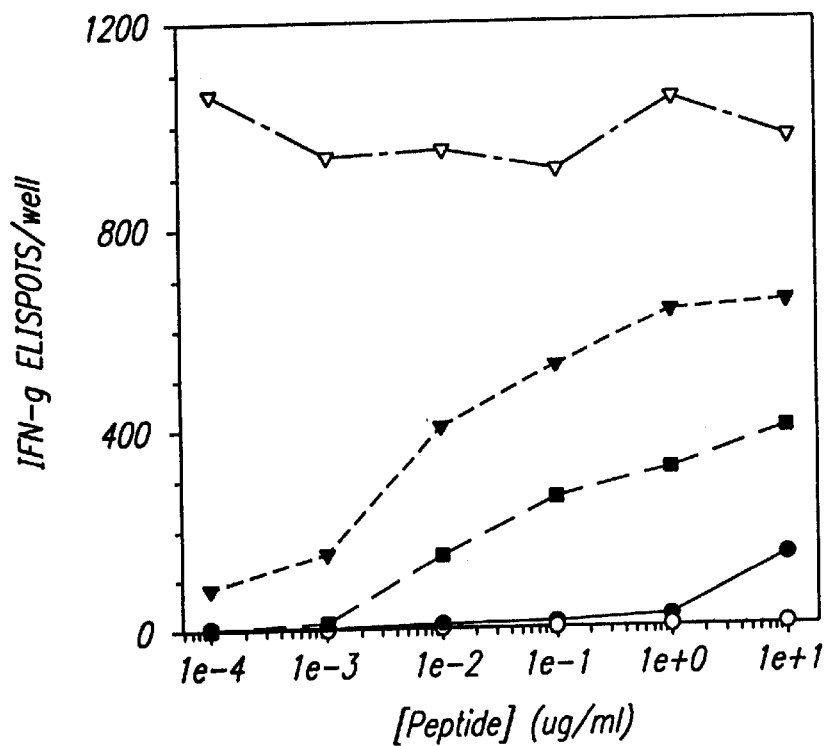
FIG. 11A is a graph showing results of an IFN-gamma ELISPOT assay, in ELISPOTS per well, as a function of peptide concentration (μg/ml). Results are shown for 5 9-mer $U_L47$ peptides tested: 548–556 (solid circles)
Figure 11B:
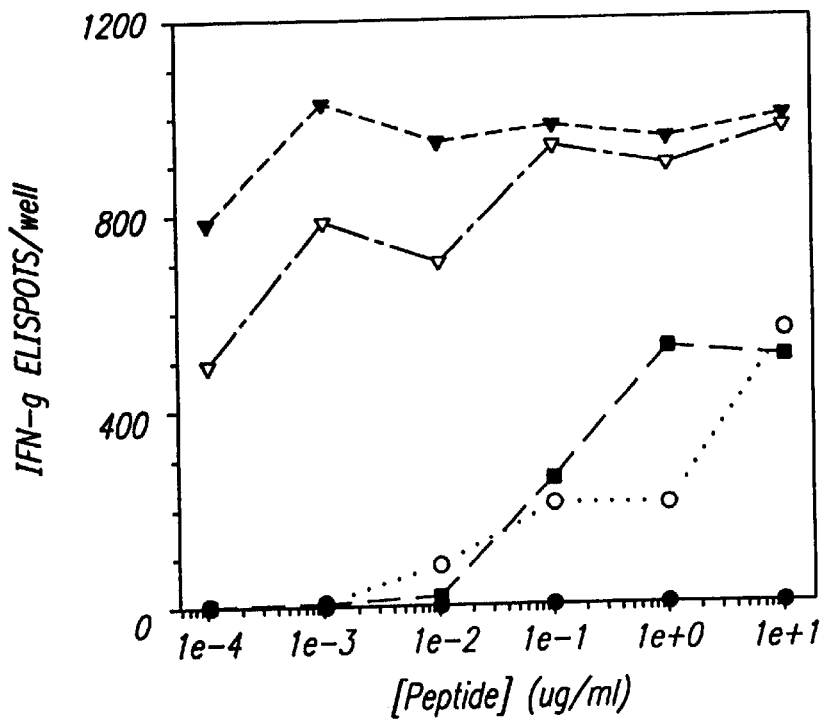

FIG. 11B is a graph showing results of an IFN-gamma ELISPOT assay, in ELISPOTS per well, as a function of peptide concentration (μg/ml). Results are shown for 5 10-mer $U_L47$ peptides tested: 548–557 (solid circles); 549–558 (open circles); 550–559 (solid triangles); 551–560 (open triangles); 552–561 (squares).

Figure 12:
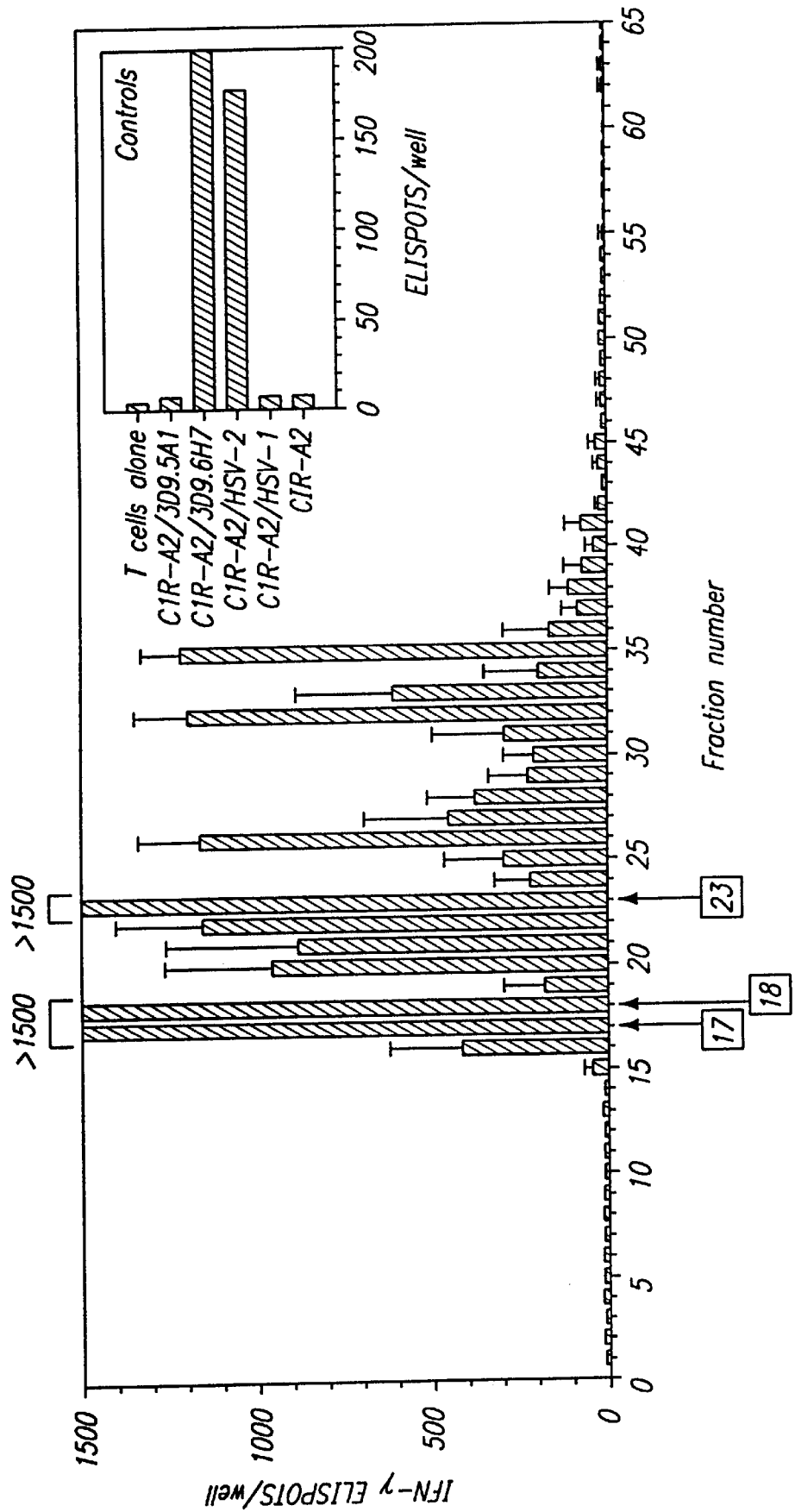

FIG. 12 is a bar graph showing results of an IFN-gamma ELISPOT assay, in ELISPOTS per well, for each of various HPLC fractions of peptides eluted from HLA-A2 on C1R-A2/3D9.6H7 cells. The results show that fractions 17, 18 and 23 contain peptides that are recognized by CTL clone cpRW22. The inset shows data for various controls, including T cells alone, C1R-A2/3D9.5A1, C1R-A2/3D9.6H7, C1R-A2/HSV-2, C1R-A2/HSV-1, and C1R-A2.

Figure 13A:
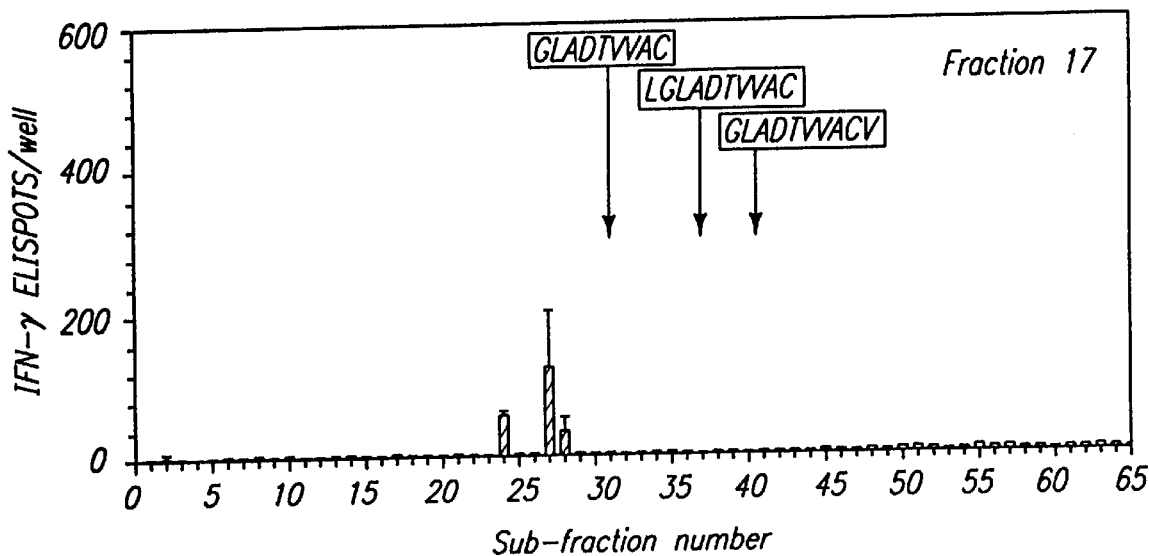

FIG. 13A is a bar graph showing results of an IFN-gamma ELISPOT assay, in ELISPOTS per well, for each of various HPLC subfractions of fraction 17. The results show that subfractions of fraction 17 contain peptides from C1RA2/3D9.6H7 that are recognized by CTL clone cpRW22. Arrows indicate peptides corresponding to SEQ ID NO: 3, 1 and 2, respectively.

Figure 13B:
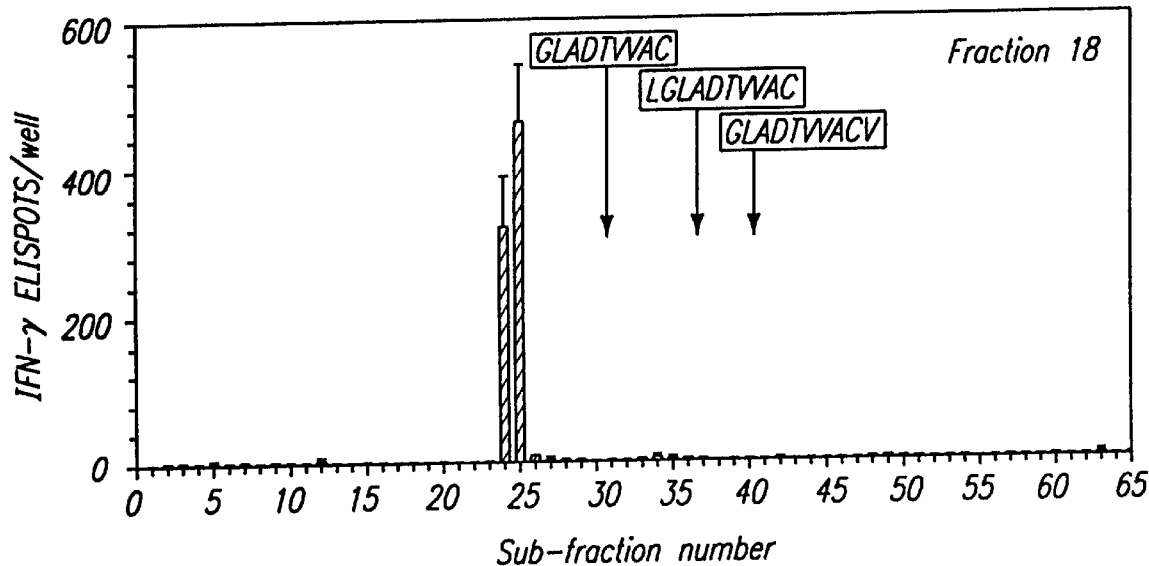

FIG. 13B is a bar graph showing results of an IFN-gamma ELISPOT assay, in ELISPOTS per well, for each of various HPLC subfractions of fraction 18. The results show that subfractions of fraction 18 contain peptides from C1R-A2/3D9.6H7 that are recognized by CTL clone cpRW22. Arrows indicate peptides corresponding to SEQ ID NO: 3, 1 and 2, respectively.

Figure 13C:
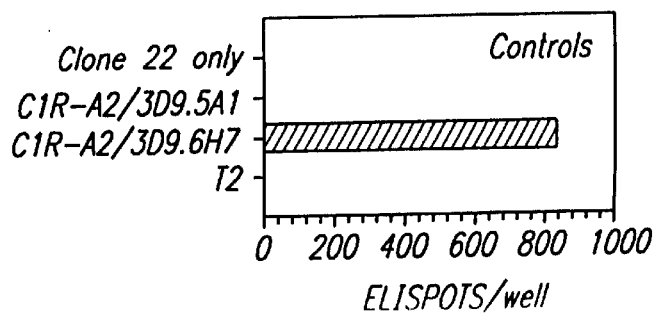

FIG. 13C is a bar graph showing results of an IFN-gamma ELISPOT assay, in ELISPOTS per well, for each of various controls: clone 22 only; C1R-A2/3D9.5A1; C1R-A2/3D9.6H7; and T2 cells.

Figure 14:
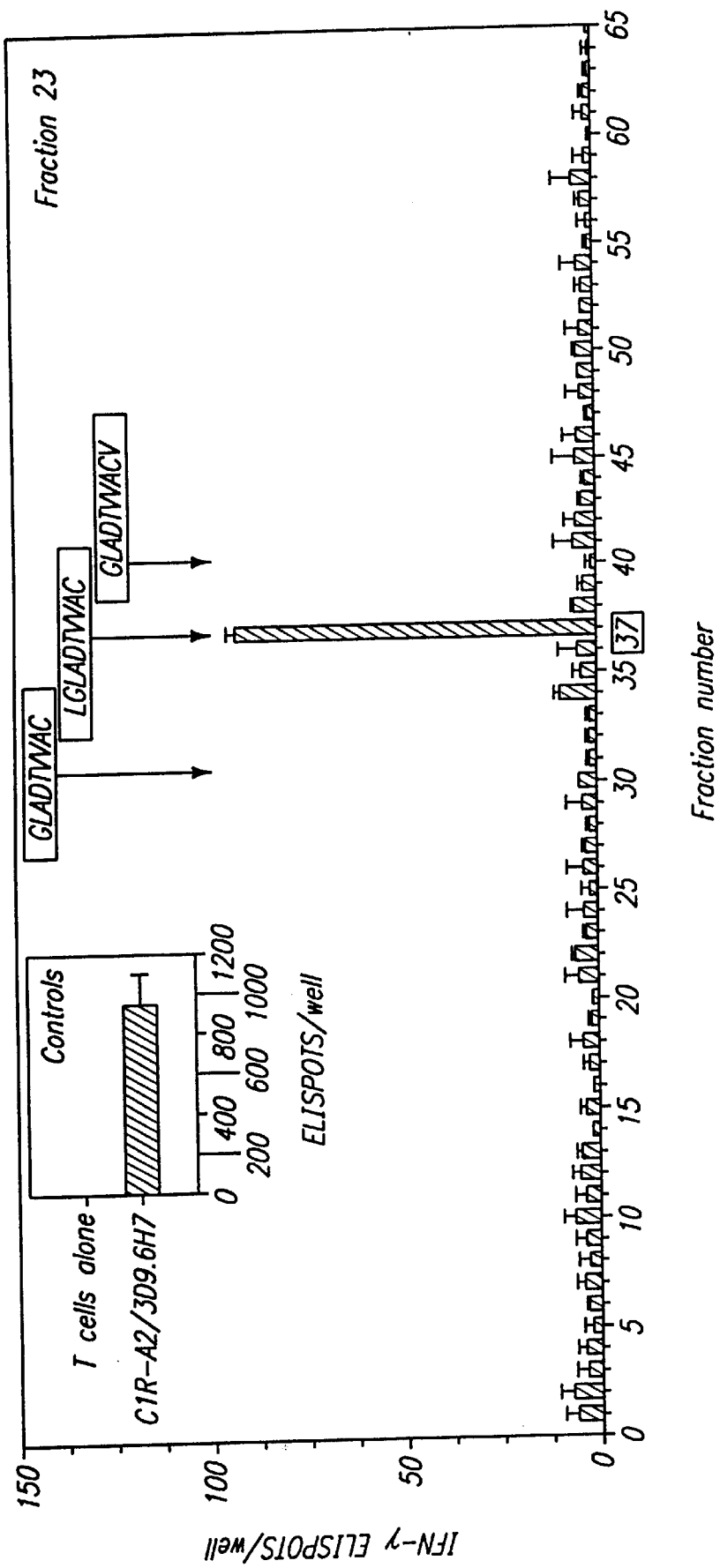

FIG. 14 is a bar graph showing results of an IFN-gamma ELISPOT assay, in ELISPOTS per well, for each of various HPLC subfractions of fraction 23 from C1R-A2/3D9.6H7 cells. The results show that subfraction 37 sensitizes T2 cells for recognition by CTL clone cpRW22. The activity in this fraction has the same mobility on HPLC as $U_L47/550$–559. Arrows indicate peptides corresponding to SEQ ID NO: 3, 1 and 2, respectively. The inset shows data for controls, including T cells alone and C1R-A2/3D9.6H7.

Figure 15A:
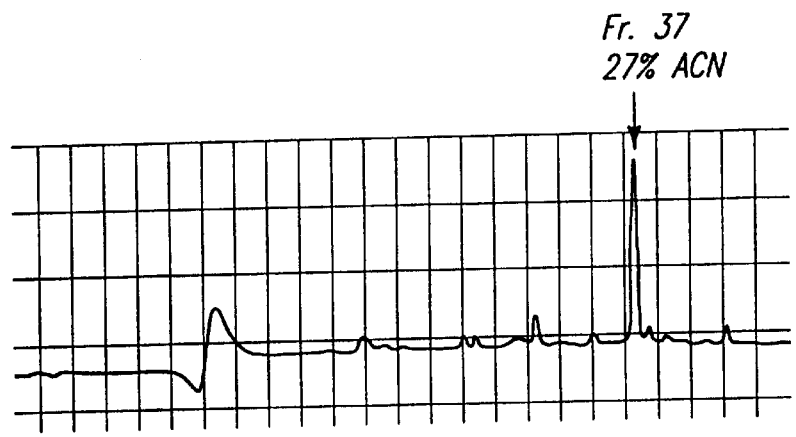

FIG. 15A shows the results of HPLC fractionation of HSV2 synthetic peptide LGLADTVVAC (SEQ ID NO: 1; $U_L47/550$–559). The peptide was run through HPLC under the subfractionation conditions and found to elute in fraction 37.

Figure 15B:
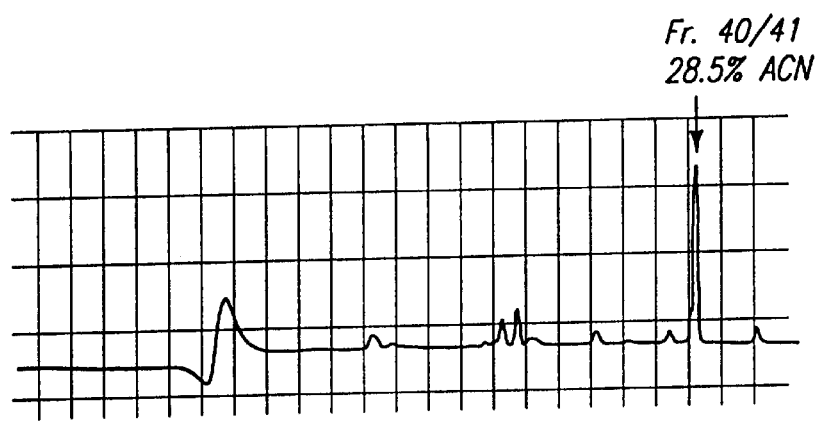

FIG. 15B shows the results of HPLC fractionation of HSV2 synthetic peptide GLADTVTACV (SEQ ID NO: 2; $U_L47/551$–560). The peptide was run through HPLC under the subfractionation conditions and found to elute in fraction 40/41.

Figure 15C:
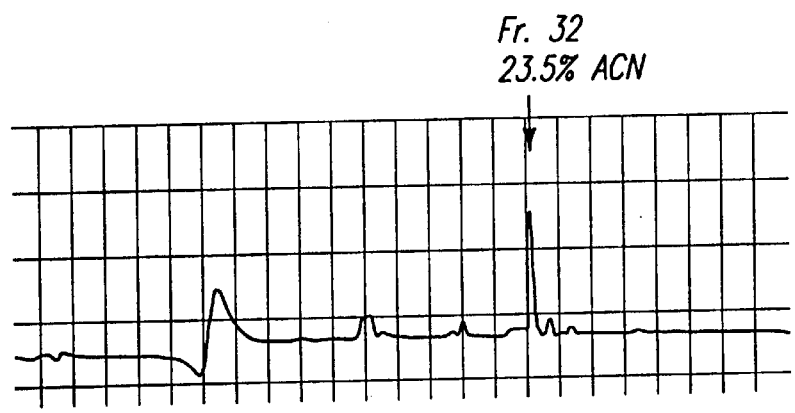

FIG. 15C shows the results of HPLC fractionation of HSV2 synthetic peptide GLADTVVAC (SEQ ID NO: 3; $U_L47/551$–559). The peptide was run through HPLC under the subfractionation conditions and found to elute in fraction 32.

Figure 16:
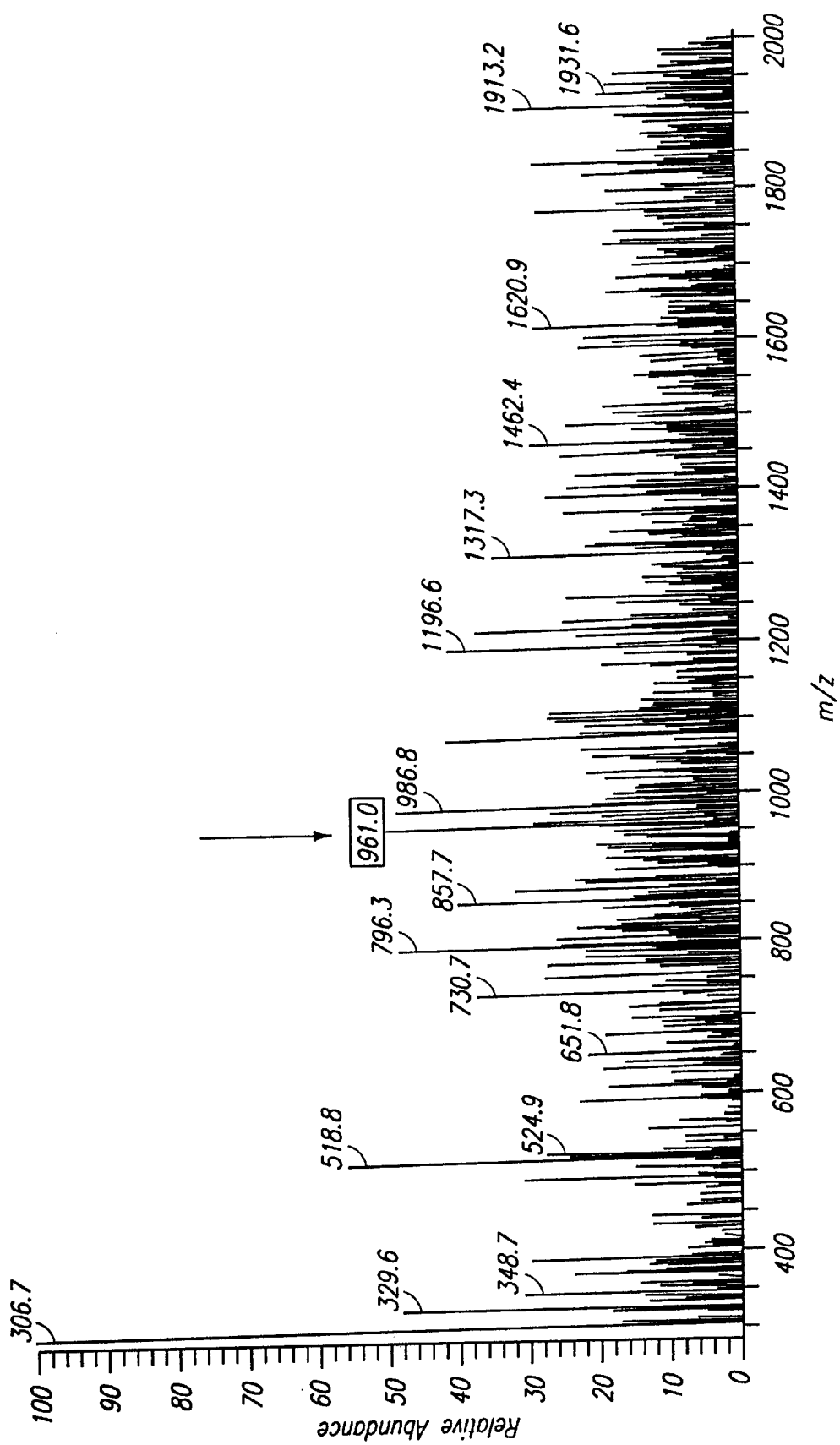

FIG. 16 shows mass spectra data, plotted as relative abundance as a function of m/z, for fraction 23/subfraction 37 from C1R-A2/3D9.6H7; These data show that a peptide with the same mass (MW=961) as $U_L47/550$–559 is present in this subfraction.

FIG. 17 shows the sequences (SEQ ID NO: 14–17) of various primers used for PCR to demonstrate that the C1R-A2/3D9.6H7 cells contain at least two retroviral inserts derived from HSV-2.

Figure 18A:
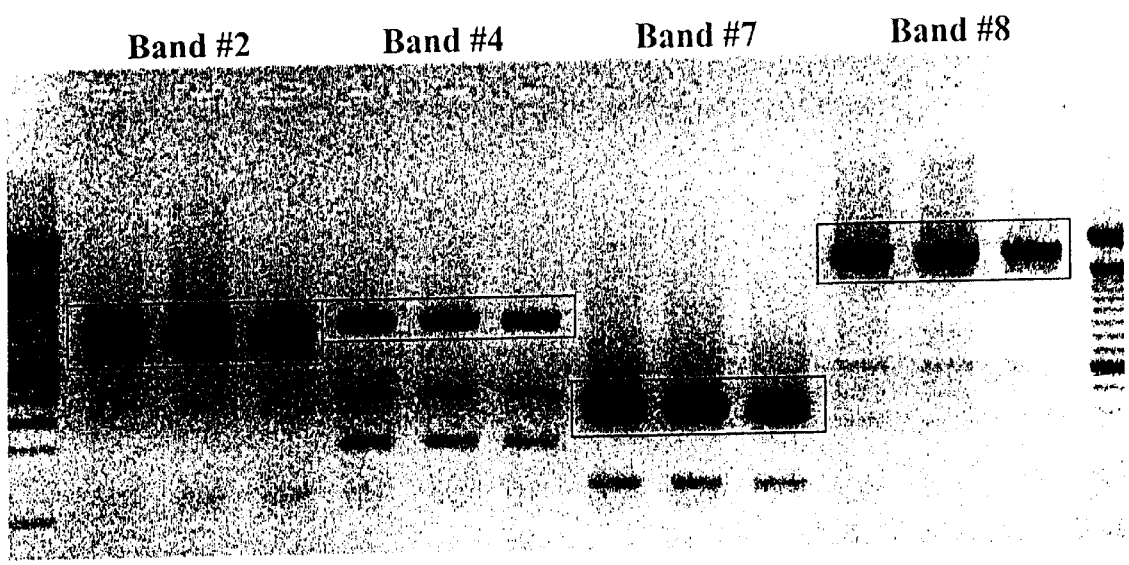

FIG. 18A shows the results of the PCR analysis of retroviral inserts from C1R-A2/3D9.6H7 cells, confirming that these cells contain inserts from HSV-2. Bands 2, 4 and 8 refer to the portions of the $U_L47$ insert illustrated in FIG. 18B; band 7 refers to the $U_L52$ insert illustrated in FIG. 18C.

Figure 18B:
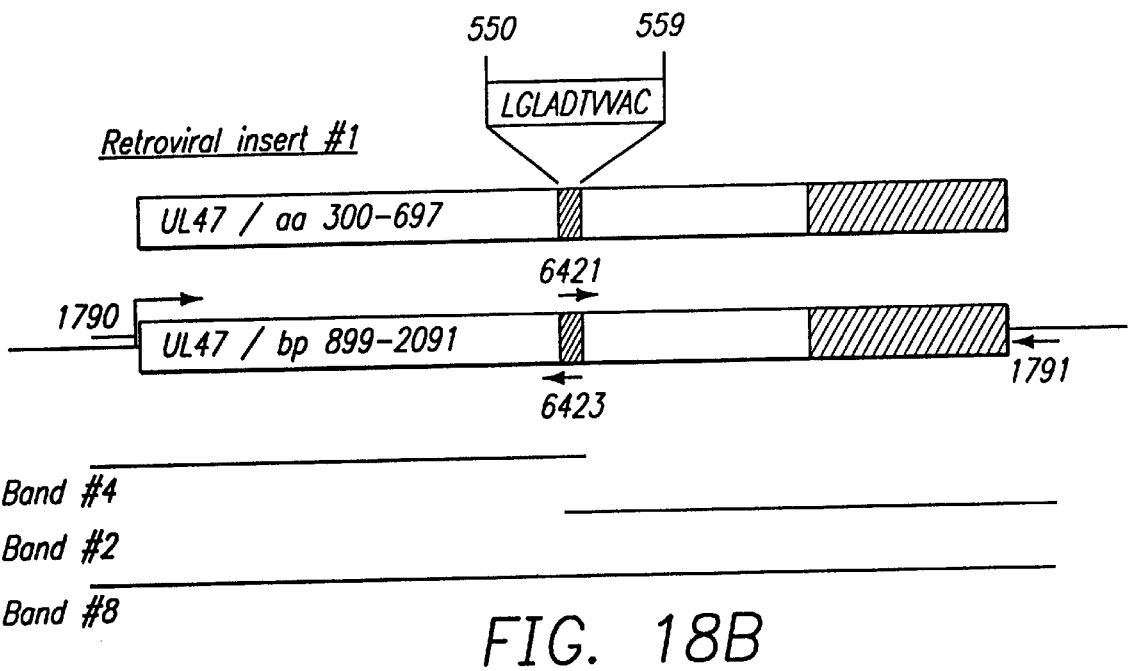

FIG. 18B is a schematic illustration of the large portion of the $U_L47$ gene encoded by a retroviral insert from C1R-A2/3D9.6H7 cells. This insert includes a portion encoding the $U_L47/550$–559 peptide (SEQ ID NO: 1).

Figure 18C:
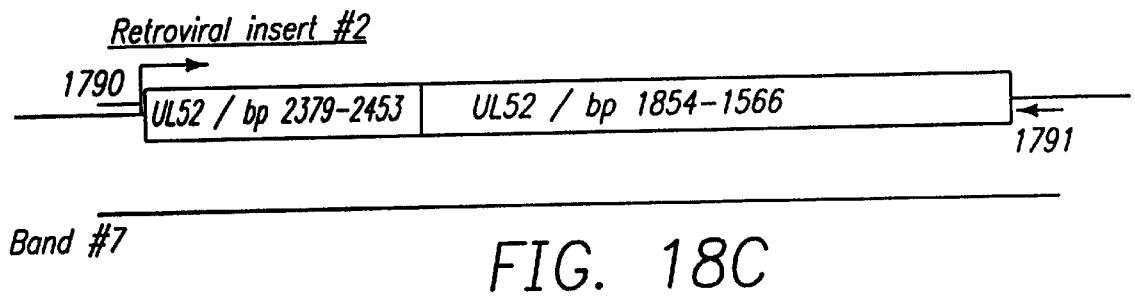

FIG. 18C is a schematic illustration of the two fragments of the $U_L52$ gene encoded by a second retroviral insert from C1R-A2/3D9.6H7 cells.

Figure 19:
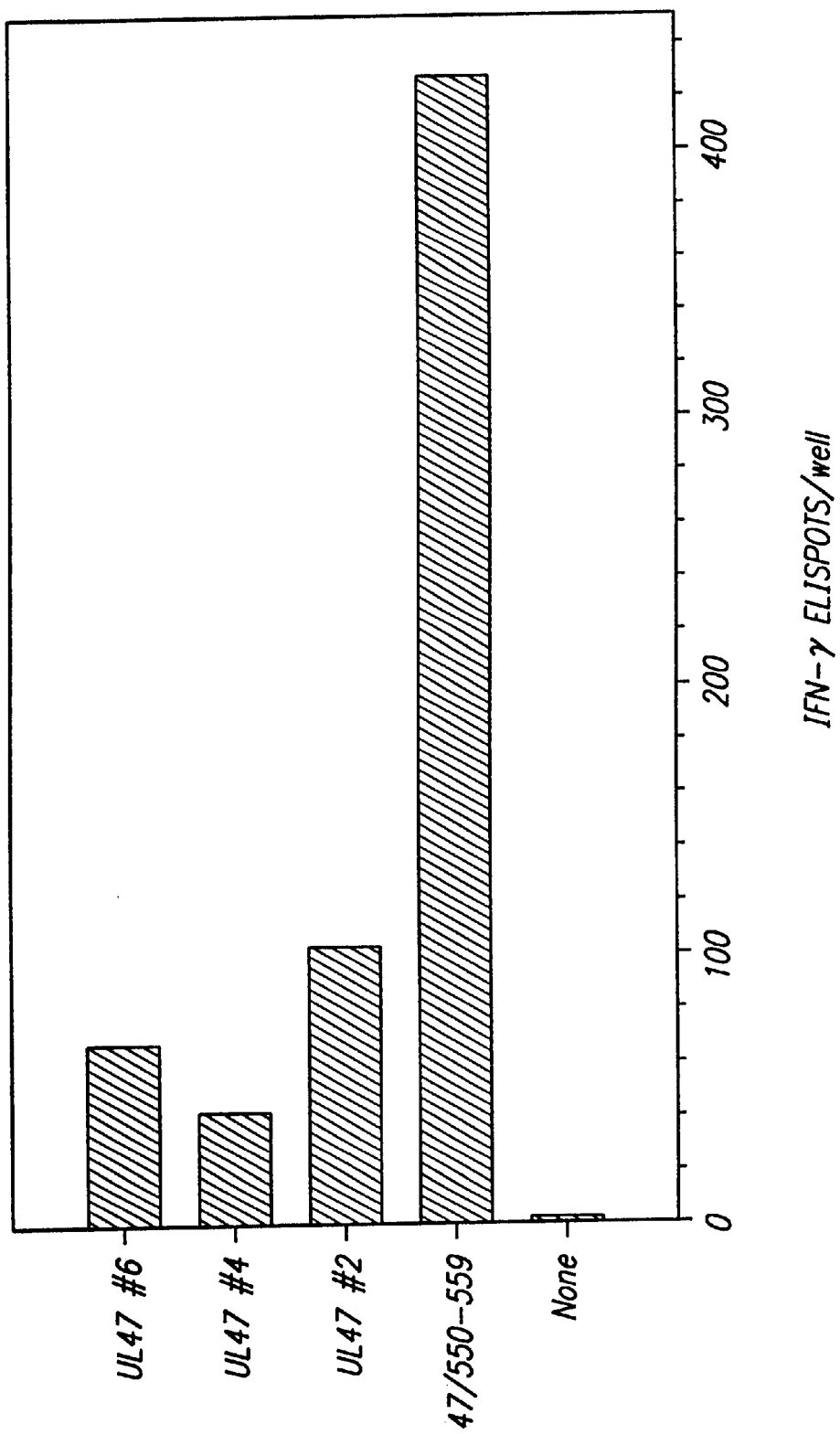

FIG. 19 is a bar graph showing that $U_L47$ gene-transfected VA13/A2 cells are recognized by CD8+ T cell clone cpRW22, as determined by interferon-gamma secretion measured in ELISPOTS/well. Targets were VA13 fibroblasts stably expressing HLA-A2. Targets were pulsed with $U_L47$ peptide or transiently transfected with $U_L47$ expression plasmid clones #2, #4 or #6. Responders were the cpRW22 CD8+ T cell clone.

FIGS. 20A–L are graphs showing CTL responses by different HLA-A2 donors, plotted as percent specific lysis as a function of effector:target ratio. Targets were pulsed with either no peptide (solid circles), the stimulating peptide (open circles), or a control peptide derived from HIV (triangles).

Figures 20A, 20B, 20C:
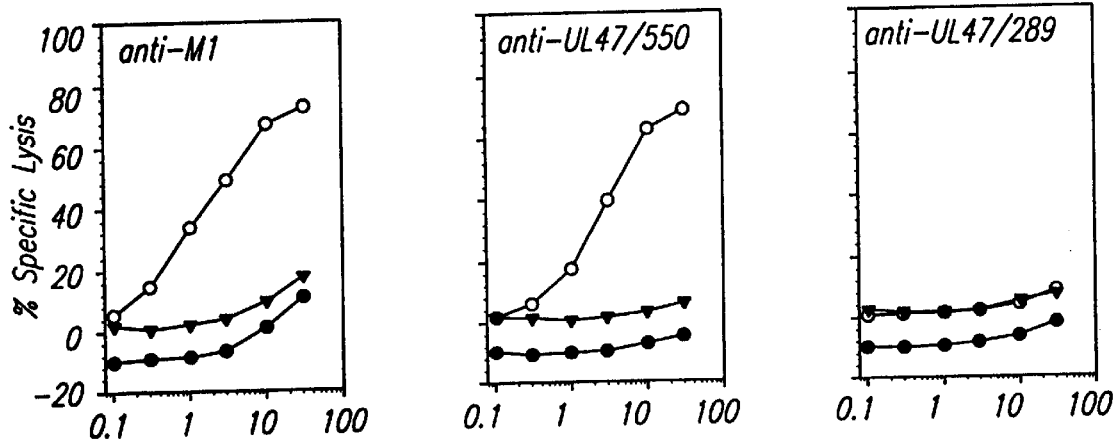

FIG. 20A shows results for donor RW1874. PBMC were stimulated with influenza M1/58–66.

FIG. 20B shows results for donor RW1874. PBMC were stimulated with $U_L47/550$–559.

FIG. 20C shows results for donor RW1874. PBMC were stimulated with $U_L47/289$–298.

Figures 20D, 20E, 20F:
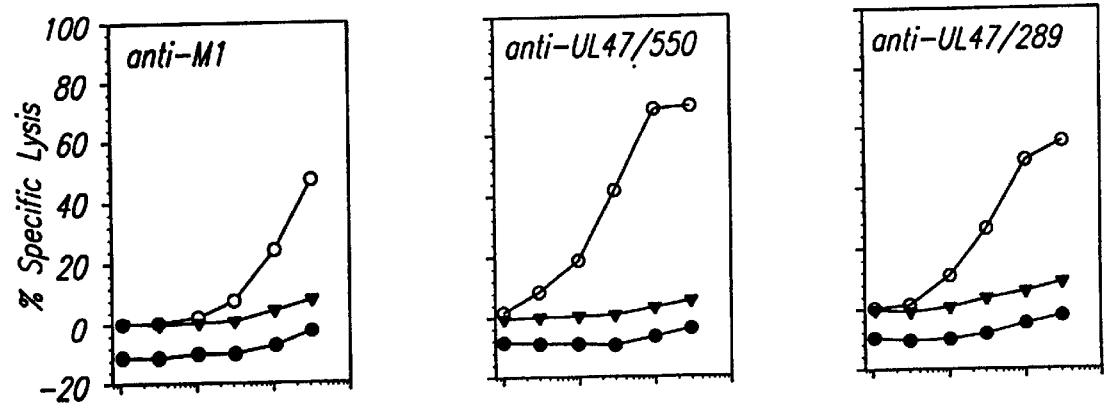

FIG. 20D shows results for donor HV5101. PBMC were stimulated with M1/58–66.

FIG. 20E shows results for donor HV5101. PBMC were stimulated with $U_L47/550$–559.

FIG. 20F shows results for donor HV5101. PBMC were stimulated with $U_L47/289$–298.

FIG. 20G shows results for donor AD120. PBMC were stimulated with M1/58–66.

FIG. 20H shows results for donor AD120. PBMC were stimulated with $U_L47/550$–559.

FIG. 20I shows results for donor AD120. PBMC were stimulated with $U_L47/289$–298.

FIG. 20J shows results for donor AD124. PBMC were stimulated with M1/58–66.

FIG. 20K shows results for donor AD124. PBMC were stimulated with $U_L47/550$–559.

FIG. 20L shows results for donor AD124. PBMC were stimulated with $U_L47/289$–298.

DETAILED DESCRIPTION OF THE INVENTION

The invention provides HSV antigens that are useful for the prevention and treatment of HSV infection. Disclosed herein are antigens and/or their constituent epitopes confirmed to be recognized by T-cells derived from herpetic lesions. In some embodiments, T-cells having specificity for antigens of the invention have demonstrated cytotoxic activity against virally infected cells. The identification of immunogenic antigens responsible for T-cell specificity facilitates the development of improved anti-viral therapeutic and prophylactic strategies. Compositions containing antigens or polynucleotides encoding antigens of the invention provide effectively targeted vaccines for prevention and treatment of HSV infection.

Definitions

All scientific and technical terms used in this application have meanings commonly used in the art unless otherwise specified. As used in this application, the following words or phrases have the meanings specified.

As used herein, "polypeptide" includes proteins, fragments of proteins, and peptides, whether isolated from natural sources, produced by recombinant techniques or chemically synthesized. Polypeptides of the invention typically comprise at least about 6 amino acids.

As used herein, "HSV polypeptide" includes HSV-1 and HSV-2, unless otherwise indicated. References to amino acids of HSV proteins or polypeptides are based on the genomic sequence information regarding HSV-2 as described in A. Dolan et al., 1998, J. Virol. 72(3):2010–2021. As noted below, the predicted polypeptide sequence of ICP0 of HSV-2 based on sequencing RNA from cells transfected with a fragment of ICP0 differs from the published sequence by the omission of amino acid Q26.

As used herein, "substitutional variant" refers to a molecule having one or more amino acid substitutions or deletions in the indicated amino acid sequence, yet retaining the ability to be specifically recognized by an immune cell. The amino acid sequence of a substitutional variant is preferably at least 80% identical to the native amino acid sequence, or more preferably, at least 90% identical to the native amino acid sequence. One method for determining whether a molecule can be specifically recognized by an immune cell is the cytotoxicity assay described in D. M. Koelle et al., 1997, Human Immunol. 53:195–205. Other methods for determining whether a molecule can be specifically recognized by an immune cell are described in the examples provided hereinbelow, including the ability to stimulate secretion of interferon-gamma or the ability to lyse cells presenting the molecule. An immune cell will specifically recognize a molecule when, for example, stimulation with the molecule results in secretion of greater interferon-gamma than stimulation with control molecules. For example, the molecule may stimulate greater than 5 pg/ml, or preferably greater than 10 pg/ml, interferon-gamma secretion, whereas a control molecule will stimulate less than 5 pg/ml interferon-gamma.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally occurring nucleotides.

As used herein, "antigen-presenting cell" or "APC" means a cell capable of handling and presenting antigen to a lymphocyte. Examples of APCs include, but are not limited to, macrophages, Langerhans-dendritic cells, follicular dendritic cells, B cells, monocytes, fibroblasts and fibrocytes. Dendritic cells are a preferred type of antigen presenting cell. Dendritic cells are found in many non-lymphoid tissues but can migrate via the afferent lymph or the blood stream to the T-dependent areas of lymphoid organs. In non-lymphoid organs, dendritic cells include Langerhans cells and interstitial dendritic cells. In the lymph and blood, they include afferent lymph veiled cells and blood dendritic cells, respectively. In lymphoid organs, they include lymphoid dendritic cells and interdigitating cells.

As used herein, "modified" to present an epitope refers to antigen-presenting cells (APCs) that have been manipulated to present an epitope by natural or recombinant methods. For example, the APCs can be modified by exposure to the isolated antigen, alone or as part of a mixture, peptide loading, or by genetically modifying the APC to express a polypeptide that includes one or more epitopes.

As used herein, "pharmaceutically acceptable salt" refers to a salt that retains the desired biological activity of the parent compound and does not impart any undesired toxicological effects. Examples of such salts include, but are not limited to, (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, furmaric acid, gluconic acid, citric acid, malic acid, ascorbic acid, benzoic acid, tannic acid, pamoic acid, alginic acid, polyglutamic acid, naphthalenesulfonic acids, naphthalene-disulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluroacetate salt and the acetate salt.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, Remington's Pharmaceutical Sciences, Chapter 43, 14th Ed., Mack Publishing Co, Easton Pa. 18042, USA).

As used herein, "adjuvant" includes those adjuvants commonly used in the art to facilitate the stimulation of an immune response. Examples of adjuvants include, but are not limited to, helper peptide; aluminum salts such as aluminum hydroxide gel (alum) or aluminum phosphate; Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham); QS-21 (Aquilla); MPL or 3d-MPL (Corixa Corporation, Hamilton, Mont.); LEIF; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; muramyl tripeptide phosphatidyl ethanolamine or an immunostimulating complex, including cytokines (e.g., GM-CSF or interleukin-2, -7 or -12) and immunostimulatory DNA sequences. In some embodiments, such as with the use of a polynucleotide vaccine, an adjuvant such as a helper peptide or cytokine can be provided via a polynucleotide encoding the adjuvant.

As used herein, "a" or "an" means at least one, unless clearly indicated otherwise.

HSV Polypeptides

In one embodiment, the invention provides an isolated herpes simplex virus (HSV) polypeptide, wherein the polypeptide comprises an ICP0 or $U_L47$ protein or a fragment thereof In one embodiment, the fragment comprises amino acids 92–101 of ICP0 or a substitutional variant thereof. In another embodiment, the fragment comprises amino acids 289–298, 548–557, 550–559, 551–559 and/or 551–561 of $U_L47$ or a substitutional variant thereof. The reference to amino acid residues is made with respect to the proteins of the HSV-2 genome as described in A. Dolan et al., 1998, J. Virol. 72(3):2010–2021.

The polypeptide can be a fusion protein. In one embodiment, the fusion protein is soluble. A soluble fusion protein of the invention can be suitable for injection into a subject and for eliciting an immune response. Within certain embodiments, a polypeptide can be a fusion protein that comprises multiple polypeptides as described herein, or that comprises at least one polypeptide as described herein and an unrelated sequence. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., 1985, Gene 40:39–46; Murphy et al., 1986, Proc. Natl. Acad. Sci. USA 83:8258–8262; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al., 1997, New Engl. J. Med., 336:86–9).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenza virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known. as amidase LYTA (encoded by the Lyta gene; Gene 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see Biotechnology 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In some embodiments, it may be desirable to couple a therapeutic agent and a polypeptide of the invention, or to couple more than one polypeptide of the invention. For example, more than one agent or polypeptide may be coupled directly to a first polypeptide of the invention, or linkers that provide multiple sites for attachment can be used. Alternatively, a carrier can be used. Some molecules are particularly suitable for intercellular trafficking and protein delivery, including, but not limited to, VP22 (Elliott and O'Hare, 1997, Cell 88:223–233; see also Kim et al., 1997, J. Immunol. 159:1666–1668; Rojas et al., 1998, Nature Biotechnology 16:370; Kato et al., 1998, FEBS Lett. 427(2):203–208; Vives et al., 1997, J. Biol. Chem. 272(25): 16010–7; Nagahara et al., 1998, Nature Med. 4(12):1449–1452).

A carrier may bear the agents or polypeptides in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088).

In general, polypeptides (including fusion proteins) and polynucleotides as described herein are isolated. An "isolated" polypeptide or polynucleotide is one that is removed from its original environment. For example, a naturally occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not part of the natural environment.

The polypeptide can be isolated from its naturally occurring form, produced by recombinant means or synthesized chemically. Recombinant polypeptides encoded by DNA sequences described herein can be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably the host cells employed are $E.\ coli$, yeast or a mammalian cell line such as Cos or CHO. Supernatants from the soluble host/vector systems that secrete recombinant protein or polypeptide into culture media may be first concentrated using. a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Fragments and other variants having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, wherein amino acids are sequentially added to a growing amino acid chain (Merrifield, 1963, J. Am. Chem. Soc. 85:2146–2149). Equipment for automated synthesis of polypeptides is commercially available from suppliers such as Perkin Elmer/Applied BioSystems Division (Foster City, Calif.), and may be operated according to the manufacturer's instructions.

Variants of the polypeptide for use in accordance with. the invention can have one or more amino acid substitutions, deletions, additions and/or insertions in the amino acid sequence indicated that result in a polypeptide that retains the ability to elicit an immune response to HSV or HSV-infected cells. Such variants may generally be identified by modifying one of the polypeptide sequences described herein-and evaluating the reactivity of the modified polypeptide using a known assay such as a T cell assay described herein. Polypeptide variants preferably exhibit at least about 70%, more preferably at least about 90%, and most preferably at least about 95% identity to the identified polypeptides. These amino acid substitutions include, but are not necessarily limited to, amino acid substitutions known in the art as "conservative".

A "conservative" substitution is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants ma y also (or alternatively) be modified by, for example, the deletion or addition of amino acids that have minimal influence on the immunogenicity, secondary structure and hydropathic nature of the polypeptide.

Polynucleotides, Vectors, Host Cells and Recombinant Viruses

The invention provides polynucleotides that encode one or more polypeptides of the invention. The polynucleotide can be included in a vector. The vector can further comprise an expression control sequence operably. linked to the polynucleotide of the invention. In some embodiments, the vector includes one or more polynucleotides encoding other molecules of interest. In one embodiment, the polynucleotide of the invention and an additional polynucleotide can be linked so as to encode a fusion protein.

Within certain embodiments, polynucleotides may be formulated so to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

The invention also provides a host cell transformed with a vector of the invention. The transformed host cell can be used in a method of producing a polypeptide of the invention. The method comprises culturing the host cell and recovering the polypeptide so produced. The recovered polypeptide can be purified from culture supernatant.

Vectors of the invention can be used to genetically modify a cell, either in vivo, ex vivo or in vitro. Several ways of genetically modifying cells are known, including transduction or infection with a viral vector either directly or via a retroviral producer cell, calcium phosphate precipitation, fusion of the recipient cells with bacterial protoplasts containing the DNA, treatment of the recipient cells with liposomes or microspheres containing the DNA, DEAE dextran, receptor-mediated endocytosis, electroporation, micro-injection, and many other techniques known to those of skill. See, e.g., Sam brook et al. Molecular Cloning—A Laboratory Manual (2nd ed.) 1–3, 1989; and Current Protocols in Molecular Biology, F. M. Ausubel et al., eds., Greene Publishing Associates, Inc. and John Wiley & Sons, Inc., (1994 Supplement).

Examples of viral vectors include, but are not limited to retroviral vectors based on, e.g., HIV, SIV, and murine retroviruses, gibbon ape leukemia virus and other viruses such as adeno-associated viruses (AAVs) and adenoviruses. (Miller et al. 1990, Mol. Cell Biol. 10:4239; J. Kolberg 1992, NIH Res. 4:43, and Cornetta et al. 1991, Hum. Gene Ther. 2:215). Widely used retroviral vectors include those based upon murine leukemia virus (MuLV), gibbon ape leukemia virus (GaLV), ecotropic retroviruses, simian immunodeficiency virus (SIV), human immunodeficiency virus (HIV), and combinations. See, e.g. Buchscher et al. 1992, J. Virol. 66(5):2731–2739; Johann et al. 1992, J. Virol. 66(5):1635–1640; Sommerfelt et al. 1990, Virol. 176:58–59; Wilson et al. 1989, J. Virol. 63:2374–2378; Miller et al. 1991, J. Virol. 65:2220–2224, and Rosenberg and Fauci 1993 in Fundamental Immunology, Third Edition, W. E. Paul (ed.) Raven Press, Ltd., New York and the references therein; Miller et al. 1990, Mol. Cell. Biol. 10:4239; R. Kolberg 1992, J. NIH Res. 4:43; and Cornetta et al. 1991, Hum. Gene Ther. 2:215.

In vitro amplification techniques suitable for amplifying sequences to be subcloned into an expression vector are known. Examples of such in vitro amplification methods, including the polymerase chain reaction (PCR), ligase chain reaction (LCR), Qβ-replicase amplification and other RNA polymerase mediated techniques (e.g., NASBA), are found in Sambrook et al. 1989, Molecular Cloning—A Laboratory, Manual (2nd Ed) 1–3; and U.S. Pat. No. 4,683,202; PCR Protocols A Guide to Methods and Applications (Innis et al. eds.) Academic Press Inc. San Diego, Calif. 1990. Improved methods of cloning in vitro amplified nucleic acids are described in U.S. Pat. No. 5,426,039.

The invention additionally provides a recombinant microorganism genetically modified to express a polynucleotide of the invention. The recombinant microorganism can be useful as a vaccine, and can be prepared using techniques known in the art for the preparation of live attenuated vaccines. Examples of microorganisms for use as live vaccines include, but are not limited to, viruses and bacteria. In a preferred embodiment, the recombinant microorganism is a virus. Examples of suitable viruses include, but are not limited to, vaccinia virus, canary pox virus, retrovirus, lentivirus, HSV and adenovirus.

Compositions

The invention provides compositions that are useful for treating and preventing HSV infection. The compositions can be used to inhibit viral replication and to kill virally-infected cells. In one embodiment, the composition is a pharmaceutical composition. The composition can comprise a therapeutically or prophylactically effective amount of a polypeptide, polynucleotide, recombinant virus, APC or immune cell of the invention. An effective amount is an amount sufficient to elicit or augment an immune response, e.g., by activating T cells. One measure of the activation of T cells is a cytotoxicity assay, as described in D. M. Koelle et al., 1997, Human Immunol. 53:195–205. In some embodiments, the composition is a vaccine.

The composition can optionally include a carrier, such as a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention. Formulations suitable for parenteral administration, such as, for example, by intraarticular (in the joints), intravenous, intramuscular, intradermal, intraperitoneal, and subcutaneous routes, and carriers include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, preservatives, liposomes, microspheres and emulsions.

The composition of the invention can further comprise one or more adjuvants. Examples of adjuvants include, but are not limited to, helper peptide, alum, Freund's, muramyl tripeptide phosphatidyl ethanolamine or an immunostimulating complex, including cytokines. In some embodiments, such as with the use of a polynucleotide vaccine, an adjuvant such as a helper peptide or cytokine can be provided via a polynucleotide encoding the adjuvant. Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other viral antigens may be present, either incorporated into a fusion polypeptide or as a separate compound, within the composition or vaccine.

A pharmaceutical composition or vaccine may contain DNA encoding one or more of the polypeptides of the invention, such that the polypeptide is generated in situ. As noted above, the DNA may be present within any of a variety of delivery systems known to those of ordinary skill in the art, including nucleic acid expression systems, bacteria and vital expression systems. Numerous gene delivery techniques are well known in the art, such as those described by Rolland, 1998, Crit. Rev. Therap. Drug Carrier Systems 15:143–198, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., 1989, Proc. Natl. Acad. Sci. USA 86:317–321; Flexner et al., 1989, Ann. My Acad. Sci. 569:86–103; Flexner et al., 1990, Vaccine 8:17–21; U.S. Pat. Nos. 4,603,112, 4,769,330, and 5,017,487; WO 89/01973; U.S. Pat. No. 4,777,127; GB 2,200,651; EP 0,345,242; WO 91102805; Berkner, 1988, Biotechniques 6:616–627; Rosenfeld et al., 1991, Science 252:431–434; Kolls et al., 1994, Proc. Natl. Acad. Sci. USA 91:215–219; Kass-Eisler et al., 1993, Proc. Natl. Acad. Sci. USA 90:11498–11502; Guzman et al., 1993, Circulation 88:2838–2848; and Guzman et al.,1993, Cit. Res. 73:1202–1207. Techniques for incorporating DNA into such expression systems are well known to those of ordinary skill in the art. The DNA may also be "naked," as described, for example, in Ulmer et al., 1993, Science 259:1745–1749 and reviewed by Cohen, 1993, Science 259:1691–1692. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophlizate. Compounds may also be encapsulated within liposomes using well known technology.

Any of a variety of adjuvants may be employed in the vaccines of this invention. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes biodegradable microspheres; monophosphoryl lipid A and quil A. Cytokines, such as GM CSF or interleukin-2, -7, or -12, may also be used as adjuvants.

Within the vaccines provided herein, the adjuvant composition is preferably designed to induce an immune response predominantly of the Th1-type. High levels of Th1-type cytokines (e.g., IFN-γ, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, 1989, Ann. Rev. Immunol. 7:145–173.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL™ adjuvants are available from Corixa Corporation (see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Another adjuvant that may be used is AS-2 (Smith-Kline Beecham). Any vaccine provided herein may be prepared using well known methods that result in a combination of antigen, immune response enhancer and a suitable carrier or excipient.

The compositions described herein may be administered as part of a sustained release formulation (ie., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets HSV-infected cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation, and/or maintenance of the T cell response, to have antiviral effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245–251, 1998) and have been shown to be effective as a physiological adjuvant for eliciting prophylactic or therapeutic immunity (see Timmerman and Levy, Ann. Rev. Med. 50:507–529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (Zitvogel et al., 1998, Nature Med. 4:594–600).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80 and CD86). APCs may generally be transfected with a polynucleotide encoding a polypeptide (or portion or other variant thereof) such that the polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., 1997, Immunology and Cell Biology 75:456–460. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides r cell help (e.g., a carrier molecule). Alternatively, a dendritic cell may be pulsed with a non-conjugated immunological partner, separately or in the presence of the polypeptide.

Administration of the Compositions

Treatment includes prophylaxis and therapy. Prophylaxis or treatment can be accomplished by a single direct injection at a single time point or multiple time points. Administration can also be nearly simultaneous to multiple sites. Patients or subjects include mammals, such as human, bovine, equine, canine, feline, porcine, and ovine animals. Preferably, the patients or subjects are human.

Compositions are typically administered in vivo via parenteral (e.g. intravenous, subcutaneous, and intramuscular) or other traditional direct routes, such as buccal/sublingual, rectal, oral, nasal, topical, (such as transdermal and ophthalmic), vaginal, pulmonary, intraarterial, intraperitoneal, intraocular, or intranasal routes or directly into a specific tissue.

The compositions are administered in any suitable manner, often with pharmaceutically acceptable carriers. Suitable methods of administering cells in the context of the present invention to a patient are available, and, although more than one route can be used to administer a particular cell composition, a particular route can often provide a more immediate and more effective reaction than another route.

The dose administered to a patient, in the context of the present invention should be sufficient to effect a beneficial therapeutic response in the patient over time, or to inhibit infection or disease due to infection. Thus, the composition is administered to a patient in an amount sufficient to elicit an effective immune response to the specific antigens and/or to alleviate, reduce, cure or at least partially arrest symptoms and/or complications from the disease or infection. An amount adequate to accomplish this is defined as a "therapeutically effective dose."

The dose will be determined by the activity of the composition produced and the condition of the patient, as well as the body weight or surface areas of the patient to be treated. The size of the dose also will be determined by the existence, nature, and extent of any adverse side effects that accompany the administration of a particular composition in a particular patient. In determining the effective amount of the composition to be administered in the treatment or prophylaxis of diseases such as HSV infection, the physician needs to evaluate the production of an immune response against the virus, progression of the disease, and any treatment-related toxicity.

For example, a vaccine or other composition containing a subunit HSV protein can include 1–10,000 micrograms of HSV protein per dose. In a preferred embodiment, 10–1000 micrograms of HSV protein is included in each dose in a more preferred embodiment 10–100 micrograms of HSV protein dose. Preferably, a dosage is selected such that a single dose will suffice or, alternatively, several doses are administered over the course of several months. For compositions containing HSV polynucleotides or peptides, similar quantities are administered per dose.

In one embodiment, between 1 and 10 doses may be administered over a 52week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an antiviral immune response, and is at least 10–50% above the basal (i.e., untreated) level. Such vaccines should also be capable of causing an immune response that leads to an improved clinical outcome in vaccinated patients as compared to non-vaccinated patients. In general, for pharmaceutical compositions and vaccines comprising one or more polypeptides, the amount of each polypeptide present in a dose ranges from about 0.1 μg to about 5 mg per kg of host. Preferably, the amount ranges from about 10 to about 1000 μg per dose. Suitable volumes for administration will vary with the size, age and immune status of the patient, but will typically range from about 0.1 mL to about 5 mL, with volumes less than about 1 mL being most common.

Compositions comprising immune cells are preferably prepared from immune cells obtained from the subject to whom the composition will be administered. Alternatively, the immune cells can be prepared from an HLA-compatible donor. The immune cells are obtained from the subject or donor using conventional techniques known in the art, exposed to APCs modified to present an epitope of the invention, expanded ex vivo, and administered to the subject. Protocols for ex vivo therapy are described in Rosenberg et al., 1990, New England J. Med. 9:570–578. In addition, compositions can comprise APCs modified to present an epitope of the invention.

Immune cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to enrich and rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or mote polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., 1997, Immunological Reviews 157:177).

Administration by many of the routes of administration described herein or otherwise known in the art may be accomplished simply by direct administration using a needle, catheter or related device, at a single time point or at multiple time points.

In Vivo Testing of Identified Antigens

Conventional techniques can be used to confirm the in vivo efficacy of the identified HSV antigens. For example, one technique makes use of a mouse challenge model. Those skilled in the art, however, will appreciate that these methods are routine, and that other models can be used.

Once a compound or composition to be tested has been prepared, the mouse or other subject is immunized with a series of injections. For example up to 10 injections can be administered over the course of several months, typically with one to 4 weeks elapsing between doses. Following the last injection of the series, the subject is challenged with a dose of virus established to be a uniformly lethal dose. A control group receives placebo, while the experimental group is actively vaccinated. Alternatively, a study can be designed using sublethal doses. Optionally, a dose-response study can be included. The end points to be measured in this study include death and severe neurological impairment, as evidenced, for example, by spinal cord gait. Survivors can also be sacrificed for quantitative viral cultures of key organs including spinal cord, brain, and the site of injection. The quantity of virus present in ground up tissue samples can be measured. Compositions can also be tested in previously infected animals for reduction in recurrence to confirm efficacy as a therapeutic vaccine.

Efficacy can be determined by calculating the $IC_{50}$, which indicates the micrograms of vaccine per kilogram body weight required for protection of 50% of subjects from death. The $IC_{50}$ will depend on the challenge dose employed. In addition, one can calculate the $LD_{50}$, indicating how many infectious units are required to kill one half of the subjects receiving a particular dose of vaccine. Determination of the post mortem viral titer provides confirmation that viral replication was limited by the immune system.

A subsequent stage of testing would be a vaginal inoculation challenge. For acute protection studies, nice can be used. Because they can be studied for both acute protection and prevention of recurrence, guinea pigs provide a more physiologically relevant subject for extrapolation to humans. In this type of challenge, a non-lethal dose is administered, the guinea pig subjects develop lesions that heal and recur. Measures can include both acute disease amelioration and recurrence of lesions. The intervention with vaccine or other composition can be provided before or after the inoculation, depending on whether one wishes to study prevention versus therapy.

Methods

The invention provides a method for treatment and/or prevention of HSV infection in a subject. The method comprises administering to the subject a composition of the invention. The composition can be used as a therapeutic or prophylactic vaccine. In one embodiment, the HSV is HSV-2. Alternatively, the HSV is HSV-1. The invention additionally provides a method for inhibiting HSV replication, for killing HSV-infected cells, for increasing secretion of lymphokines having antiviral and/or immunomodulatory, activity, and for enhancing production of herpes-specific antibodies. The method comprises contacting an HSV-infected cell with an immune cell directed against an antigen of the invention, for example, as described in the Examples presented herein. The contacting can be performed in vitro or in vivo. In a preferred embodiment, the immune cell is a T cell. T cells include CD4 and CD8 T cells. Compositions of the invention can also be used as a tolerizing agent against immunopathologic disease.

In addition, the invention provides a method of producing immune cells directed against HSV. The method comprises contacting an immune cell with an antigen-presenting cell, wherein the antigen-presenting cell is modified to present an antigen included in a polypeptide of the invention. Preferably, the antigen-presenting cell is a dendritic cell. The cell can be modified by, for example, peptide loading or genetic modification with a nucleic acid sequence encoding the polypeptide. In one embodiment, the immune cell is a T cell. T cells include CD4 and CD8 T cells. Also provided are immune cells produced by the method. The immune cells can be used to inhibit HSV replication, to kill HSV-infected cells, in vitro or in vivo, to increase secretion of lymphokines having antiviral and/or immunomodulatory activity, to enhance production of herpes-specific antibodies, or in the treatment or prevention of HSV infection in a subject.

The invention provides methods for identifying immunogenic epitopes associated with infectious organisms. In one embodiment, the method comprises preparing a collection of random fragments of the organismal genome. The preparing can comprise digesting the entire genome, although it is not necessary to begin with the full genome. The digesting preferably comprises contacting the genome with one or more restriction enzymes to obtain a collection of random fragments having a desired range of lengths. Alternatively, one can sonicate, nebulize or otherwise treat material containing the genome of interest and isolate from a gel fragments of an appropriate size.

The digesting, and the selection of restriction enzymes, is designed to obtain fragments of the genome that are longer than the average length of a T cell epitope, e.g., greater than about 30 nucleotides in length. Preferably, the fragments are small enough such that genetic stops are infrequent, e.g., about 200 to about 500 base pairs in length. Where the genomic sequence or a restriction map of an organism of interest is known, one can analyze the genome to identify restriction sites that, if targeted with the appropriate restriction enzymes, will result in the desired number of fragments of an appropriate length. The restriction enzymes can also be selected to target sites that are compatible with sites in a cloning vector to be used.

The random fragments can then be used to express polypeptides encoded by the fragments. The fragments can be expressed individually, or preferably, as a pool of polypeptides, either alone or as fusion proteins. Those skilled in the art will appreciate that polypeptides can be expressed from either DNA or RNA as a starting material. For example, expression of polypeptides from RNA viruses can be achieved by first preparing a cDNA from the RNA fragment, and then using the cDNA to express the polypeptide.

The polypeptide can be expressed from a vector containing the fragment of genome. In a preferred embodiment, the vector is a plasmid, such as a pcDNA3.1 (+)his vector. Those skilled in the art will appreciate that other vectors can be used that are capable of expressing polypeptide from an insert. Preferably, the polypeptide is expressed as a fusion protein. In one embodiment, the expressing comprises culturing a host cell transfected or transduced with a vector containing the fragment of genome. In a preferred embodiment of the method, fragments are ligated into expression vectors in the three different reading frames, and in both directions, to make a library.

The quality of the library can be improved by ligating the genomic fragments using a partial fill-in reaction. For example, the sticky ends created by digestion of HSV-2 with Sau3A I can result in ligation of multiple viral fragments to one another and in a variety of orientations. A partial fill-in reaction can be used to modify the sticky ends such that the fragments of viral genome will not ligate to each other, and only one viral insert will be present in each vector. This results in a library that is simpler and less time-consuming to analyze.

The method further comprises assaying the ability of the expressed polypeptide to elicit an immune response. The ability to elicit an immune response is indicative of the presence of an immunogenic epitope within the polypeptide. In one embodiment, the immune response is a cellular immune response. The assaying can comprise performing an assay that measures T cell stimulation or activation. Examples of T cells include CD4 and CD8 T cells.

One example of a T cell stimulation assay is a cytotoxicity assay, such as that described in Koelle, DM et al., Human Immunol. 1997, 53;195–205. In one example, the cytotoxicity assay comprises contacting a cell that presents the antigenic viral peptide in the context of the appropriate HLA molecule with a T cell, and detecting the ability of the T cell to kill the antigen presenting cell. Cell killing can be detected by measuring the release of radioactive $^{51}Cr$ from the antigen presenting cell. Release of $^{51}Cr$ into the medium from the antigen presenting cell is indicative of cell killing. An exemplary criterion for increased killing is a statistically significant increase in counts per minute (cpm) based on counting of $^{51}Cr$ radiation in media collected from antigen presenting cells admixed with T cells as compared to control media collected from antigen presenting cells admixed with media.

The assay can be performed on pools of polypeptides to identify pools containing active moieties. Further assays can then be performed on increasingly smaller subsets of the original pools to isolate polypeptides of interest. The material containing a fragment of interest, e.g., a plasmid with its viral insert, can be purified and the viral fragment sequenced. Based on the obtained sequence information, synthetic peptides can be prepared for subsequent testing and confirmation of the identified antigens. Sequencing of fragments can also lead to the identification of novel genes. The foregoing method steps can be repeated, wherein subfragments of the genome fragments are prepared. Increasingly smaller fragments can be expressed and tested to determine the minimal epitope.

The method of the invention can be applied to a variety of infectious organisms, including bacteria, parasites and viruses. Preferred viruses are those containing intronless DNA or mostly coding sequence. Examples of viruses include double-stranded DNA viruses, single-stranded DNA viruses, double-stranded RNA viruses and single-stranded RNA viruses. Examples of double-stranded DNA viruses include, but are not limited to, Epstein-Barr virus (EBV), cytomegalovirus (CMV), herpes simplex virus-1 (HSV-1), HSV-2, varicella-zoster virus (VZV), human herpes virus-6 (HHV-6), HHV-7, HHV-8, poxvirus and adenovirus.

Examples of single-stranded DNA viruses include, but are not limited to, parvovirus. Examples of double-stranded RNA viruses include, but are not limited to, retroviruses and reoviruses. Examples of single-stranded RNA viruses include, but are not limited to, paramyxoviruses, myxoviruses, and flaviviruses.

Because the method does not require knowledge of the organism's nucleic acid sequence, it provides a strategy for combating infectious organisms that display a great deal of biological variability (e.g., HIV and HCV). For viruses exhibiting high variability, it is advantageous to use a source of viral nucleic acid material derived from a particular patient, a particular site (e.g., blood, skin, cervix) or representative viral strain circulating in a particular geographical region or patient population, which may differ from prototypical strains of known nucleic acid sequence.

In a preferred embodiment, the organism is HSV-2 and the fragments of viral genome are prepared by digestion with Sau3A I. Examples of other restriction enzymes that can be used include, but are not limited to, Apa I, Sma I, and Alu I. The fragments of genomic DNA are then ligated into a vector, preferably by using a partial fill-in reaction (see 1999 Stratagene catalog, page 56). A preferred vector is a member of the pcDNA3.1 (+) his series. The fragments are then expressed using conventional techniques. Preferably, the expression is performed using a Cos-7 transfection method (De Plaen E et al. In: Lefkowits I, ed. Immunology Methods Manual, v. 2. New York: Academic Press, 1997:691–718).

The host cell can be co-transfected with a nucleic acid molecule, such as cDNA, encoding a relevant HLA molecule, such as an HLA heavy chain. The HLA molecule enables a host cell from a species (e.g., monkey in the case of Cos cells) differing from that of the T cell source to recognize the antigen derived from the infectious agent. The HLA molecule is selected to match the HLA molecule capable of presenting the target antigen. Methods for identifying the appropriate HLA molecule are described in Koelle, D M et al., J. Infectious Dis. 1994, 169:956–961; and DePlaen, E et al. In Immunology Methods Manual, 1997, Academic Press, 704–705. In the absence of a definitive identification of the presenting HLA molecule, cDNA encoding two or more candidate class I HLA molecules can be co-transfected.

The ability of the expressed polypeptide to elicit a cellular immune response is then assayed. Ability to elicit a cellular immune response is indicative of the presence of an immunogenic epitope. Assays that can be used to detect ability to elicit a cellular immune response include, but are not limited to, cytotoxicity assays and lymphokine secretion assays. In one embodiment, the assay is an interferon-gamma assay.

In a preferred embodiment, the invention provides a method for identifying HSV epitopes immunogenic for CD8+ T cells. The method comprises obtaining CD8+ T cells from an HSV lesion, and assaying the obtained T cells to identify-T cells having ability to recognize HSV-infected cells. The method further comprises obtaining and fragmenting a nucleic acid preparation from HSV, expressing one or more fragments of the obtained nucleic acid, and assaying the expressed fragments for antigenic reactivity with the identified HSV-specific T cells. An expressed fragment having reactivity with the HSV-specific T cells is identified as encoding an HSV epitope immunogenic for CD8+ T cells.

The invention also provides a diagnostic assay. The diagnostic assay can be used to identify the immunological responsiveness of a patient suspected of having a herpetic infection and to predict responsiveness of a subject to a particular course of therapy. The assay comprises exposing T cells of a subject to an antigen of the invention, in the context of an appropriate APC, and testing for immunoreactivity by, for example, measuring IFNγ, proliferation or cytotoxicity. Suitable assays are described in more detail in the Examples.

EXAMPLES

The following examples are presented to illustrate the present invention and to assist one of ordinary skill in making and using the same. The examples are not intended in any way to otherwise limit the scope of the invention.

Example 1

Detection of HSV-specific CD8 CTL in Recurrent Genital HSV-2 Lesions

This example demonstrates that specific CD8 CTL localize to genital HSV-2 lesions. This is shown by serial lesion biopsy studies of recurrent genital HSV-2 lesions using cells that have encountered antigen/APC in situ and are not restimulated with antigen in vitro prior to readout assays.

Materials & Methods

Lesion-infiltrating lymphocytes (LIL) were expanded for one cycle with phytohemaglutinin (PHA) and IL-2 in the presence of 50 $\mu$M acyclovir (ACV). Typically, $5 \times 10^6 - 5 \times 10^7$ cells were obtained after two weeks. The phenotype of these bulk populations has been described (Koelle D M et al., J. Clin. Invest. 1998;101:1500–1508). Among TCR αβ, CD3+ cells, there is a gradual shift to CD8 predominance as lesions mature and cultures become negative.

Results

The local response had high levels of NK-cell activity as determined by lysis of K562 and allogeneic, HSV-2 infected lymphocyte continuous line (LCL) as early as day two of symptoms. NK cells were selectively enriched in cells expanded from lesions compared to normal skin. HSV-specific CD4 cells were similarly enriched early. Lesions were enriched in both "Th1" (interferon-gamma (IFN-γ), IL-12 p40, IL-2) and "Th2" (IL-4, IL-5, IL-10, IL-13) mRNAs (Van Voorhis W C et al., J. Infect. Dis. 1996;173:491–95). The cytokine pattern of lesion-infiltrating HSV-2-specific CD8 CTL includes interferon-gamma.

In contrast to CD4 and NK activities, HSV-specific CTL infiltrated recurrent HSV-2 genital lesion at later times (typically days 5–9) and their presence correlated with virus clearance (Koelle D M et al., J. Clin. Invest. 1998;101:1500–1508). The CD4 and CD8 components were studied by subtracting NK and then either CD4 or CD8 cells. CTL activity was observed in either CD8 cells alone or in both subsets. EBV-transformed LCL (Tigges M A et al., J. Virol. 1992;66:1622–34) were used as target cells in CTL assays because autologous cells are conveniently made, HSV undergoes complete lytic replication in these cells, and high levels of HLA and co-stimulatory/adhesion molecules are present.

HSV-specific CD8 clones (Table 1) have been isolated from herpetic vesicle fluid (Koelle D M et al., J. Infect. Dis. 1994;169:956–61) and lesions (Koelle D M et al., J. Clin. Invest. 1998;101:1500–1508). Secondary restimulation with antigen was not used. Many (>1,000) microcultures of CD8-enriched cells were cloned at 0.3–2 cells/well by standard methods (Koelle D M et al., J. Clin. Invest. 1998;101:1500–1508) and ~200 clones were screened in CTL assays against autologous LCL with and without 18 hour infection with HSV-2 (multiplicity of infection, or MOI, 10). All clones were CD3/8/T CR αβ (+) and CD4/TCR γδ (−) by flow cytometry.

TABLE 1

Cytolytic activity of CD8 T cell clones (TCC) from recurrent HSV-2 lesions. Lysis is percent specific release at an effector:target (E:T) ratio of 20:1 or lower.

| Sub-ject | Bx Date | TCC | % specific lysis | | | Epitope location[1] | HLA restriction[2] |
|---|---|---|---|---|---|---|---|
| | | | Mock | HSV-1 | HSV-2 | | |
| RW | 1997 | 51 | 0 | 1 | 87 | 0.0–0.12 | B*4501 |
| RW | 1991 | 22[3] | 0 | 2 | 54 | 0.66–0.72 | A*0201 |

[1]Location of epitope within standard map (Dolan A et al., J. Virol. 1998; 72: 2010–21) of HSV-2 genome; epitope mapping for HSV-2 type-specific TCC uses HSV-1 X HSV-2 intertypic recombinant viruses (IRV) (Preston VG et al., J. Virol. 1978; 28: 499–517) as described (Koelle DM et al., J. Virol. 1994; 68: 2803–10; Koelle DM et al., J. Virol. 1998; 72: 7476–83). Boundaries are approximate.
[2]HLA allele restricting killing of HSV-2 infected, partially matched LCL as described (Koelle DM et al., J. Infect. Dis. 1994; 169: 956–61); serologic or DNA definitions as permitted by method of typing.
[3]dkRW22. RW22 and RW.1991.22 refer to a T cell clone derived from subject RW in 1991. Two clones given the designation "22" were separately derived from RW in 1991. Throughout this application, the two separately derived clones are distinguished by dkRW22 and cpRW22.

Figure 1A:
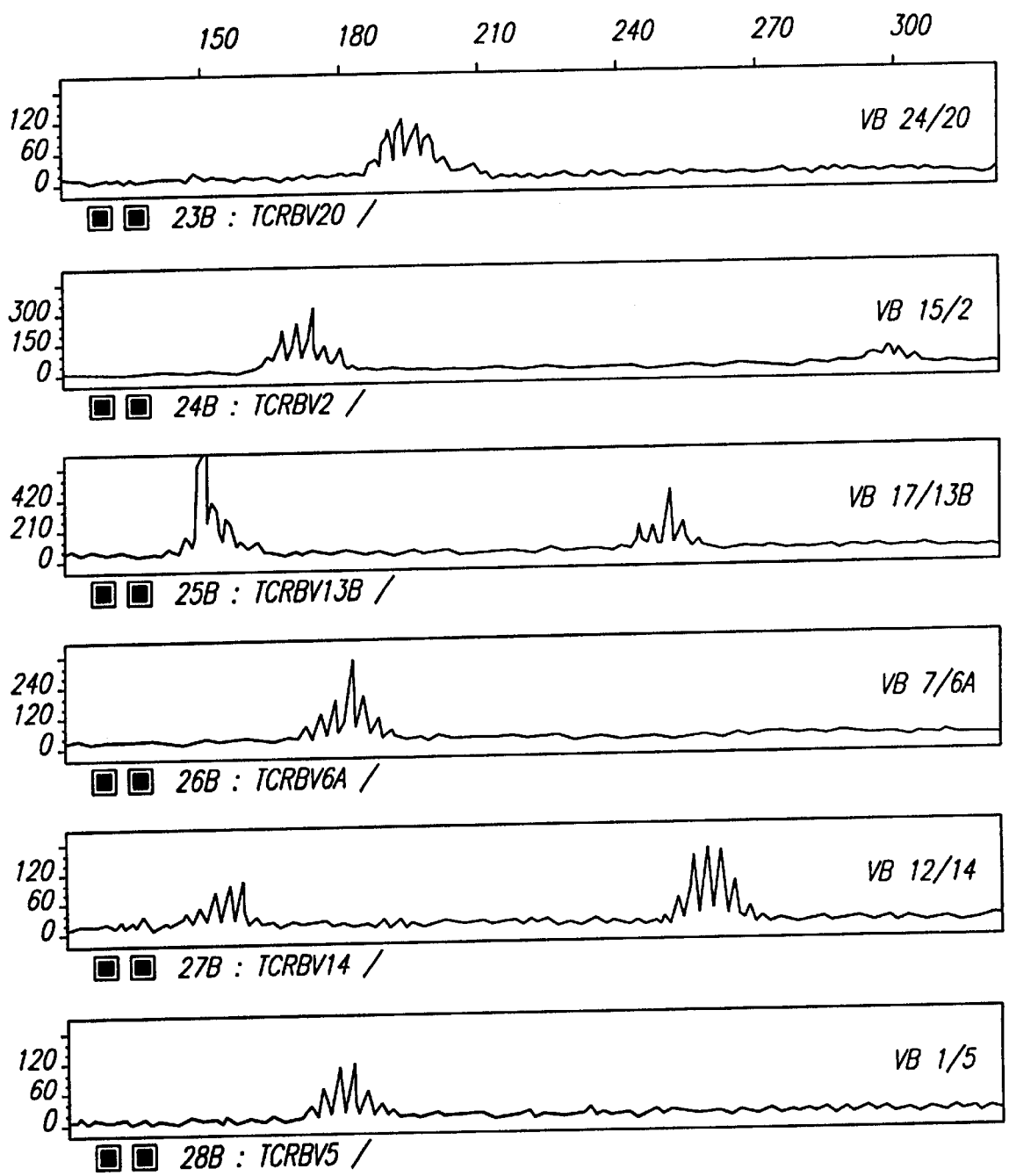
FIG. 1A shows fluorescence detection of TCR Cβ-Vβ PCR products (12 of 24 Vβ families shown) in bulk CD8-enriched PBMC from subject RW. Two Vβ primers (indicated) were used per panel in duplex analysis. X axis: molecular weights of PCR products shown at TOP based on fluorescent markers. Y axis: relative fluorescence intensity.
Figure 1B:
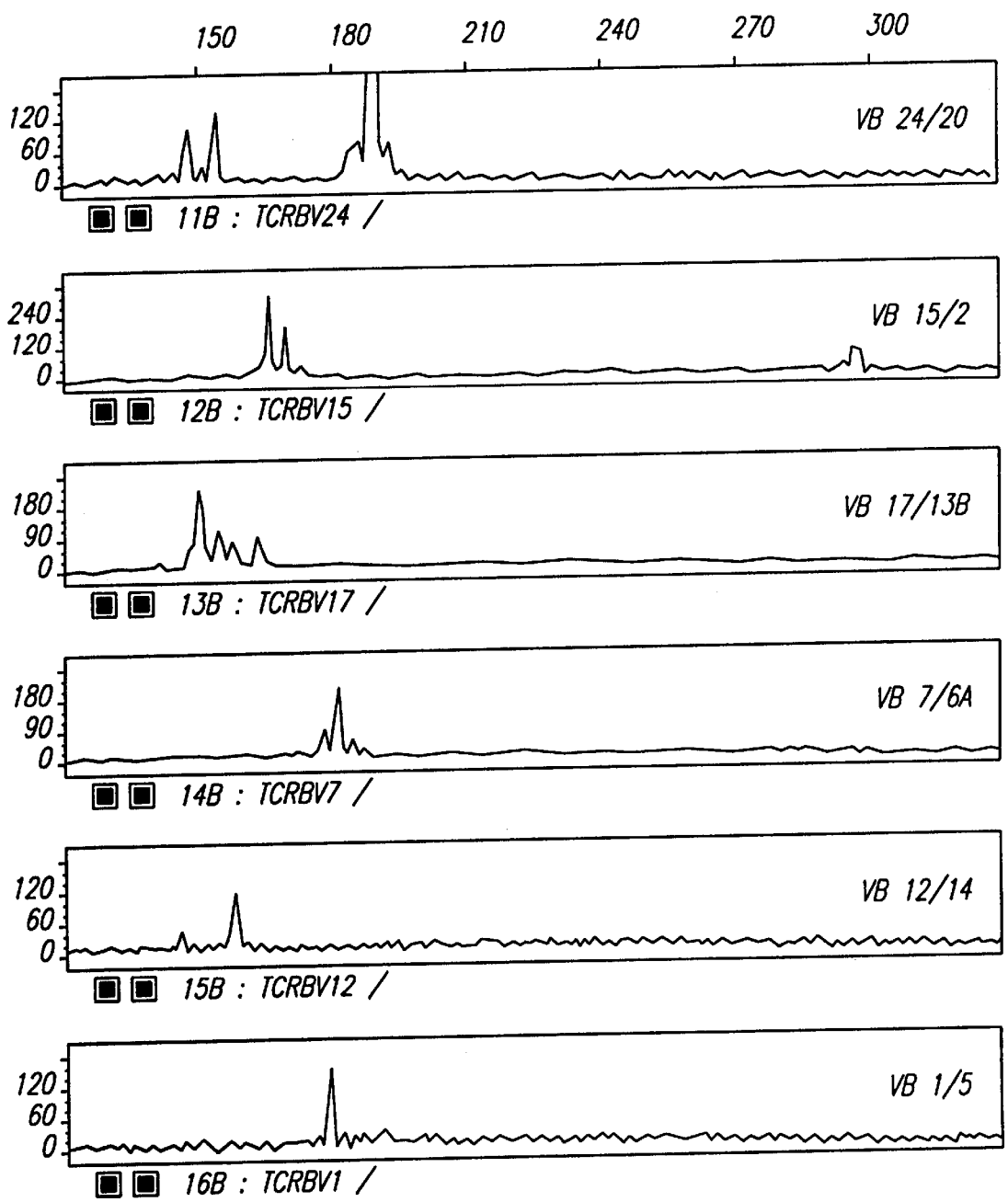
FIG. 1B shows fluorescence detection of TCR Cβ-Vβ PCR products (12 of 24 Vβ families shown) in bulk CD8-enriched lesion-infiltrating lymphocytes (LIL) from primary HSV-2 biopsy. Two Vβ primers (indicated) were used per panel in duplex analysis. X axis: molecular weights of PCR products shown at TOP based on fluorescent markers. Y axis: relative fluorescence intensity.

To measure diversity of the CD8 response, TCR Vβ analysis was performed on bulk, positively. selected CD8+ cells from LIL expanded one cycle with PHA (the source culture for CD8 CTL clone RW51, Table 1 and below), as well as CD8 cells from PBMC from the same donor. Total RNA (Chomczynski P et al., in: Coligan J E et al., eds. Current Protocols in Immunology. New York: John Wiley and Sons, 1992:10.11.7–10.11.14) was reverse transcribed with oligo-dT primer and MMLV RT (Pharmacia). cDNA was used in 24 separate PCR reactions with Cβ primer and family-specific VP primers. After 30 cycles of PCR, an aliquot of each reaction was mixed with a fluorescent-labeled internal cβ primer and PCR continued for five cycles to label amplimers of rearranged TCRVβ genes. Primers and protocols were as described in Pannetier C et al., in: Oksenberg J R, ed. The antigen T cell receptor: selected protocols and applications. New York: Chapman and Hall, 1998:Section 9. Analysis by ABI sequencer with fluorescent MW markers was done at the Biotechnology Core at Fred Hutchinson Cancer Research Center (Seattle, Wash.). The CD8 PBMC were very polyclonal as judged by the Poisson distribution and multiple peaks within the TCR Vβ amplimer "ladders" (FIG. 1A), while the lesion CD8 population appeared to be quite oligoclonal (FIG. 1B). Similar results were obtained for another donor. These data are consistent with limited diversity of the local CD8 response in HSV-2 lesions.

Example 2

Detection of HSV-specific T-cell Responses in Cervical Lymphocytes

Mucosal immune responses are segregated from PBMC, and localization of HSV-specific CTL to the mucosa of mice is associated with protection from vaginal inoculation. This example demonstrates that HSV-specific T cells, including CD8+ cells, can be detected in cervical lymphocytes.

Figure 2A:
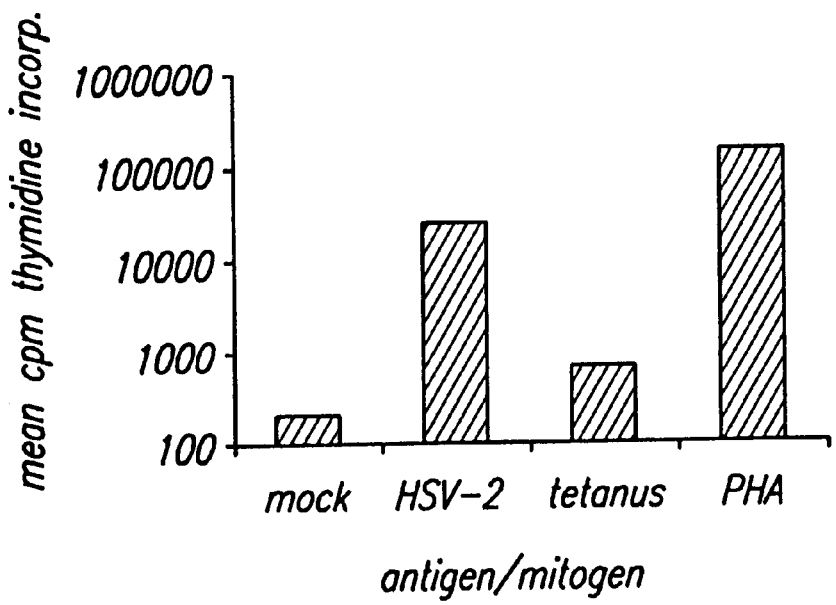
FIG. 2A shows proliferative responses of bulk-expanded cervical cytobrush-derived lymphocytes.
Figure 2B:
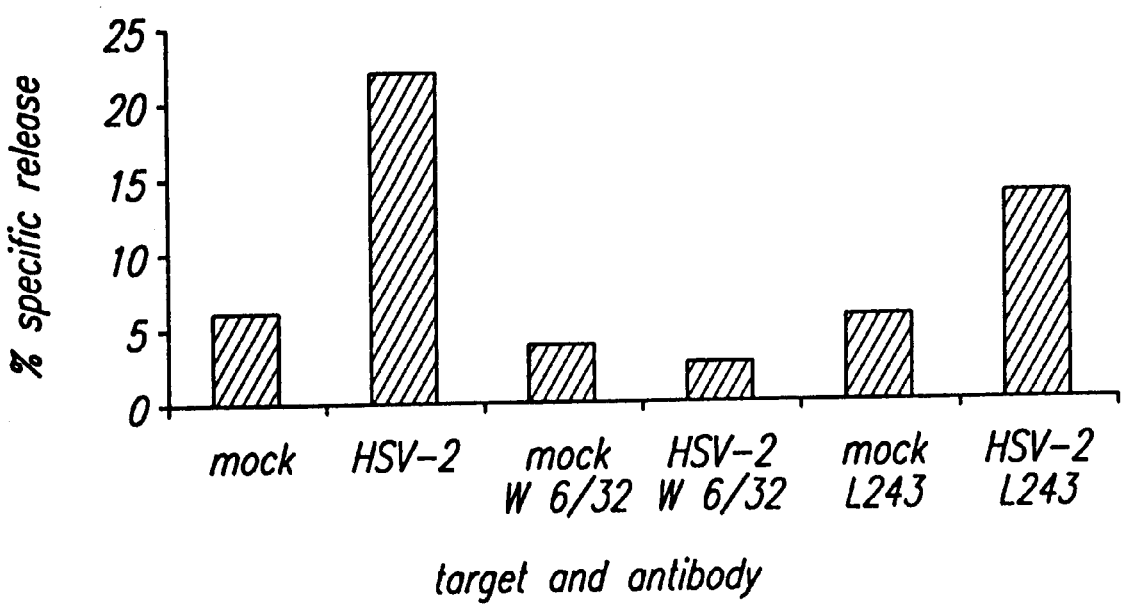
FIG. 2B shows cytotoxic responses of bulk-expanded cervical cytobrush-derived lymphocytes, plotted as percent specific release.

Cells from a representative cervical cytobrush specimen were collected during an active genital HSV-2 outbreak and expanded in bulk with PHA/IL-2, and subsequently analyzed for HSV-specific proliferative (FIG. 2A) and cytotoxic responses (FIG. 2B). Proliferation and cytotoxicity assays used autologous PBMC or LCL as APC as described above for skin-derived lymphocytes. Anti-HLA class I mAb W6/32 or anti-HLA DR mAb L243 were used as described (Koelle D M et al., J. Virol. 1994, 68:2803–10; Koelle D M et al., J. Infect. Dis. 1994, 169:956–61). Antigen-specific proliferative responses and cytotoxic responses were present. Fractionation and mAb inhibition studies show a contribution of CD8 CTL to the cytotoxic response.

Example 3

Detection of HSV-specific T-cell Responses in Primary Genital HSV-2 Lesions

In this example, biopsy specimens were collected from a patient presenting with symptoms consistent with primary genital HSV-2 infection. The phenotypes of the collected cells were determined, and LIL and PBMC from the specimens were subjected to proliferative and cytotoxicity assays. The results show that the HSV-specific proliferative and cytotoxic responses of CTL present in primary genital HSV-2 lesions are typical of those detected during recurrent disease.

CW7477 developed dysuria, fever, buttock, and lower abdomen lesions three days after his last sexual contact. Lesions lasted 13 days and grew HSV-2. Acyclovir treatment was begun on day four of symptoms. Biopsies were done on days four and seven. Serostatus was atypical positive (only a few bands present on immunoblot) at day four, with more bands, but still less than most convalescent sera, on day 26, by enhanced chemiluminescence (ECL; Dalessio J. and Ashley R., J. Clin. Microbiol. 1992, 30(4):1005–7) variant of type-specific HSV-2 immunoblot. The clinical and laboratory data were consistent with primary genital HSV-2 infection. Biopsy specimens were obtained on day four and seven of symptoms and bulk LIL expanded with PHA/IL-2 as described above.

The phenotype of the expanded cells was split between CD4 and CD8 cells, with 15–25% CD3+/CD16,56+ cells and 5–10% TCR γδ+ cells in the LIL. In comparison, cells from normal skin had almost no CD16,56 (+) events and no TCR γδ cells. The nature of the CD3+/CD16,56+ cells is unknown but these are frequently seen in expanded LIL. The antibody cocktail has a combination of αCD16-PE and αCD56-PE.

TABLE 2

Functional activity of bulk LIL or PBMC from human primary genital HSV-2 infection.

| | proliferation[1] | | | | cytotoxicity[2] | | | |
|---|---|---|---|---|---|---|---|---|
| | responder | | | | | effector | | |
| antigen | day 4 lesion | day 7 lesion | day 4 normal skin | day 15 PBMC | target | day 4 lesion | day 7 lesion | day 4 normal skin | day 4 lesion CD8+ |
| media | 203 | 587 | 153 | 1,092 | au mock | 2.9 | 2.2 | 4.3 | 1.1 |
| mock virus 1:100 | 187 | 775 | 146 | 1,296 | au HSV-1 | 16.2 | 28.3 | 2.9 | |
| UV HSV-1 1:100 | 12,926 | 26,328 | 143 | | au HSV-2 | 48.3 | 29.8 | 4.4 | 67.5 |
| UV HSV-2 1:100 | 12,685 | 14,481 | 152 | 20,179 | au vac wt | −2.5 | 4.8 | 2.3 | |
| gB2 1 µg/ml | 16,416 | 23,351 | 234 | 15,282 | au vgB2 | 15.8 | 16.8 | −5.2 | |
| gD2 1 µg/ml | 8,750 | 13,392 | 216 | 3,976 | au vgD2 | 5.1 | 13.1 | 2.1 | |
| VP16 1 µg/ml | 816 | 8,689 | 166 | | au vVP16 | 3.0 | 6.6 | 2.1 | |
| PHA 0.8 µg/ml | 12,795 | 22,318 | 41,229 | 59,691 | al mock | 1.0 | 5.9 | 2.8 | |
| | | | | | al HSV-2 | 3.6 | 4.5 | 2.7 | |
| | | | | | K562 | 1.1 | 69.2 | 2.1 | 10.4 |

[1]Bulk cells were used at $10^4$/well with autologous irradiated PBMC ($10^5$/well) as APC. Results are mean cpm $^3$H thymidine incorporation on day 4. Day 15 PBMC used at $10^5$ live cells/well.
[2]Bulk cells used at 20:1 effector:target ratio in $^{51}$Cr release versus autologous (au) or HLA mismatched (al) LCL infected 18 h., MOI 10 as indicated (v = vaccinia). CD8+ cells enriched by MidiMacs ™ (Miltenyi). Results are % specific release; spontaneous release < 22%.

The HSV-specific proliferative and cytotoxic responses were fairly typical of those detected during recurrent disease (Koelle D M et al., J. Clin. Invest. 1998; 101:1500–1508). Cross-reactive responses to HSV-1 and HSV-2 were present, as were antigen-specific responses to HSV glycoproteins. Normal skin responses were low, and PBMC responses were developing by day 15.

Example 4

Identification of an ICP0 Antigen Recognized by HSV-specific CD8 CTL

This example demonstrates, via expression cloning, the antigenicity of ICP0. In particular, an epitope within amino acids 92–101 of ICP0 is identified. In addition, the antigenicity of ICP0 is confirmed using vaccinia. The amino acid numbering uses the nomenclature and numbering of Dolan et al., J. Virol 1998, 72:2010–21.

Materials & Methods

The Cos-7 expression cloning method of Boon et al. was used for expression cloning (De Plaen E et al. In: Lefkowits I., ed. Immunology Methods Manual, v. 2. New York: Academic Press, 1997, 691–718). Interferon-gamma secretion was tested as a CD8 T-cell readout by plating $1\times10^4$ washed autologous LCL stimulators (mock- or HSV-2 infected at MOI 10 for 18 hours) and $5\times10^4$ responder TCC in triplicate for 24 hours in 200 µl TCM (Tigges M A et al., J. Virol. 1992, 66:1622–34).

Libraries used pcDNA3.1 (+)his A, B, and C (Invitrogen) as expression vectors. These specific vectors have an intrinsic ATG start 5' to the multiple cloning site (MCS), yielding fusion proteins of a leader peptide and a viral polypeptide fragment. There is a ⅙ chance any viral DNA fragment will be forward and "in-frame" with the ATG. Therefore, three vectors (A, B, and C) are used with an extra 0,1, or 2 bp between ATG and the MCS.

Libraries were made from HSV-2 strain HG52 DNA purified (MacLean A R. In: Brown S M, MacLean A R, eds. Methods in Molecular Medicine: Herpes Simplex Virus Protocols, v. 10. Totowa, N.J.: Humana Press Inc., 1998, 19–25) from Vero cells. The ~155,000 bp genome was digested with Sau3A I, predicted to give 456 fragments averaging several hundred bp long. Ends were partially filled-in and fragments ligated to Xba I-digested, partially filled-in, dephosphorylated A, B, and C vectors in separate reactions for primary libraries. Partial fill-in prevents ligation of >1 insert/vector. Contamination with cell DNA was not detected in 20 random clones. Primary libraries were amplified immediately and saved as aliquots. The goal of six-fold genomic oversampling was met, assuming each library was only ⅙ forward and in-frame: each primary library had >15,000 transformants. Three thousand clones per library were studied. Libraries were titered and diluted to 15 clones/well in deep microtiter plates. DNA was purified (Millipore 96-well format; silica chemistry) after 18 hr rotation at 300 rpm, 37° C. Yields averaging 10 µg/well (spectrophotometer) were obtained, enough for many future screens.

Lesion clone RW51 (Table 1) was chosen for expression cloning. The HLA restricting allele of CD8 TCC RW51 is B45 as LCL matched only at B45 were lysed in CTL assays. HLA B*4501 cDNA was cloned by RT-PCR. cDNA synthesis used total RNA from RW LCL (Chomczynski P, Sacchi N. In: Coligan J E et al., eds. Current Protocols in Immunology. New York: John Wiley and Sons, 1992, 10.11.7–10.11.14), oligo-dT primer and MMLV RT (Pharmacia) with standard protocols (Sambrook J et al., Molecular Cloning: a laboratory manual, v. 2, New York:

Cold Spring Harbor Press, 1989). HLA B*4501 PCR product (primers AA<u>GGTACC</u>ATGCGGGTCACGG CACCCCGAA and GG<u>TCTAGA</u>AGTTCGACACTCTCTGTGTAGT; Kpn I and Xba I sites marked; SEQ ID NO: 4 and 5, respectively) was digested, cloned into pcDNA 3.0, and sequenced. It was identical to Genbank 61710 for B*4501. Expression was checked with FITC-labeled, allele-specific mAb B12 (One Lambda, Inc.). At 48 hours, 40% of transfected (Fugene 6, Boehringer Mannheim) Cos-7 expressed surface HLA B45 by flow cytometry compared to <1% for vector. HLA A*0201, the restricting allele for CD8 TCC RW3 and dkRW22 (Table 3), was similarly cloned and expression documented with mAb MA2.1 (McMichael A J et al., Human Immunol. 1980, 1:121–29).

To screen libraries for the antigenic protein, Cos-7 cells plated (7,000/well) in flat microtiter plates were co-transfected after 24 hours with library pool and B*4501 DNA (50 and 25 ng/well). Cloned RW51 T-cells ($5 \times 10^4$/well) were added 48 hours later. Supernatant (24 additional hours) interferon-gamma ELISA (lower limit of detection, ~2 pg/ml) was done with matched mAb pair (Endogen). Two to four positive pools were found in each reading frame library (A, B, and C). Bacteria from positive pools were plated, colonies picked, and DNA made for the next round of assay. All positive clones had identical 1164 bp HSV-2 Sau3A I inserts (FIG. 3) containing exon 1, intron 1, and some of exon 2 of the HSV-2 ORF encoding IE protein ICP0. Another 445 bp of genomic DNA 5' to the ATG start of ICP0 was present. Representative positive clone A1:H3:B8 was selected for further study.

The positive genomic clones in both A and B reading register libraries, and the presence of three stop codons in-frame with the vector ATG and preceding the ICP0 ATG in both the A and B library positive clones, argues for use of the HSV-2 promoter rather than the vectors' CMV promoter. Constitutive promoter activity by 5' elements in the absence of VP16 (αTIF) and the "viral context" can occur for HSV-1 ICP0.

Figure 3:
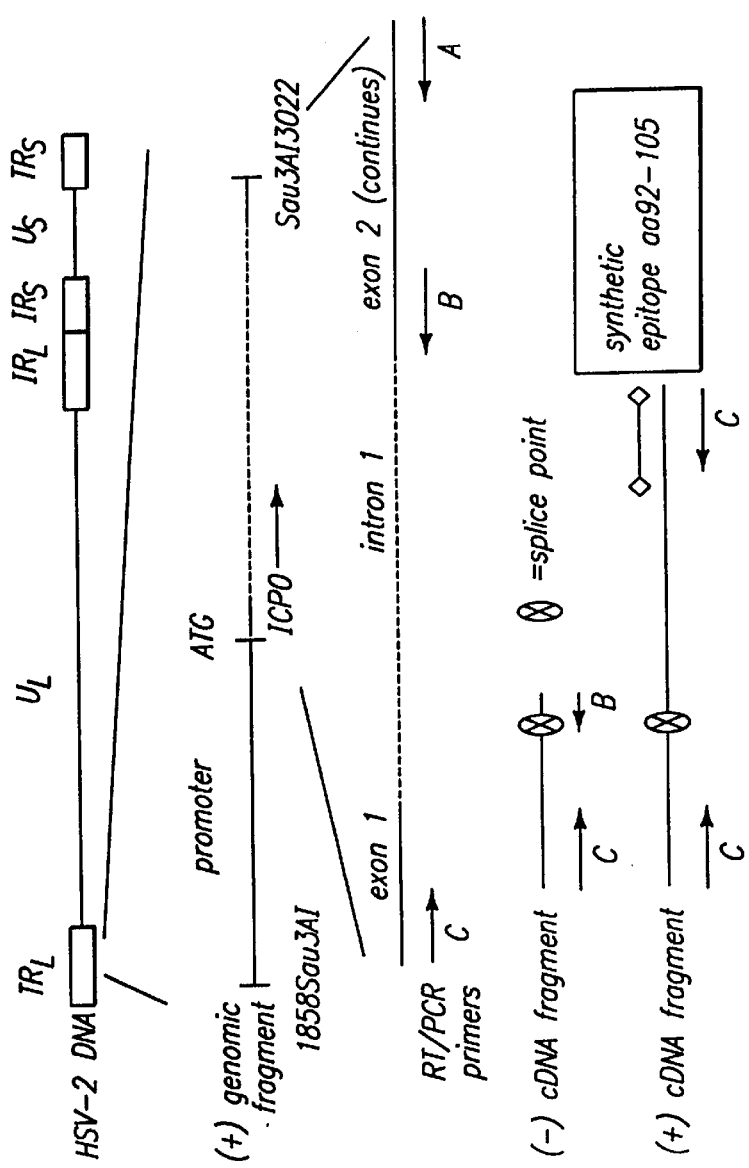
FIG. 3 is a schematic representation of the positive genomic clone isolated from Sau3A I library of HSV-2 DNA (second line), which contained part of the ICP0 gene. The genomic clone was transfected into cells and primer A used for cDNA synthesis. The exon-1/exon2 C-A (fifth line) and HLA B45 cDNAs stimulated interferon-gamma secretion from T cell clone (TCC) RW51 after transfection into Cos-7 cells. Exon-1 B-C cDNA (fourth line) was negative.

To find the epitope, an examination was made as to whether and how HSV-1 ICP0 mRNA was spliced in the Cos-7 cells. ICP0 mRNA is one of a few spliced HSV genes; alternative splicing has been reported. Total RNA from Cos-7 cells transfected with the (+) genomic fragment A1:H3:B8 (Table 4) and MMLV RT were used to make cDNA with primer C (FIG. 3). Primers A at the translational start and primer C were then used in PCR. The sequences of eight cDNA clones all showed splicing. The acceptor site was 3 bp 3' to the published site, removing amino acid Q26. To narrow down the epitope, A-C (exon1, start of exon 2) and A-B (exon 1) PCR products were cloned into the proper pcDNA3.1-based vector for in-frame expression. The exon-1–exon 2 clone was positive but the exon 1 clone was negative (Table 4) when tested for reactivity with T-cell clone RW51.

Figure 4:
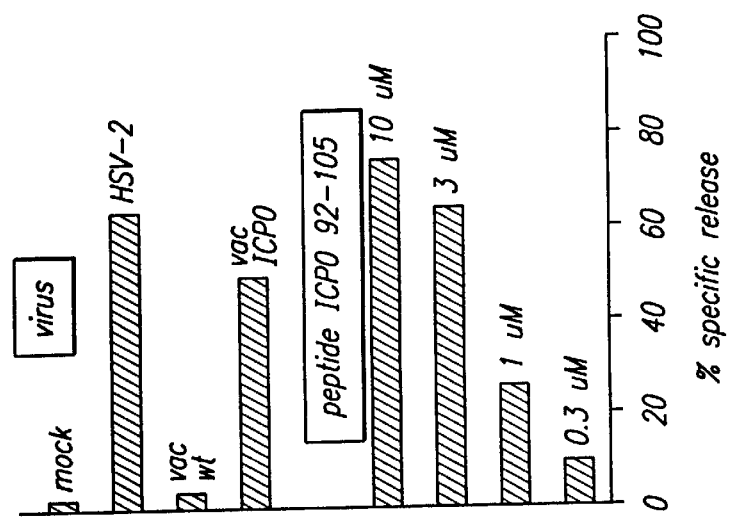
FIG. 4 is a bar graph showing CTL activity of RW51 against vaccinia ICP0 and indicated concentrations of synthetic ICP0 92–105. Four-hour $^{51}$Cr release assay with effector:target ratio 10:1. Spontaneous release all <20%.

A vaccinia-ICP0 (Manickan, E et al., J. Virol. 1995, 69(8):4711–4716) was used to confirm the expression cloning identification of ICP0 (FIG. 4).

Results

All HSV-specific CD8 clones released IFN-γ in a specific manner (Table 3). In addition, the utility, of the interferon-gamma assay was examined as a confirmatory test for HLA restriction. Clone RW51 specifically released interferon-gamma after exposure to Cos-7 cells transfected with HLA B*4501, but not with A*0201, and infection with HSV-2 (Table 3).

TABLE 3

Interferon-gamma secretion (pg/ml by ELISA) from lesion-derived HSV-specific CD8+ TCC (RW51).

| stimulator | responder TCC |
|---|---|
| autologous LCL mock | <5 |
| autologous LCL HSV-2 | 440 |
| Cos-7 A*0201/HSV-2 | <5 |
| Cos-7 B*4501/HSV-2 | 600 |

TABLE 4

Secretion of interferon-gamma of CD8 TCC RW51 in response to Cos-7 cells transfected with various DNAs (or peptide loaded at 1 μM) measured by ELISA in pg/ml. Responses of $5 \times 10^4$ TCC to $7 \times 10^3$ Cos-7 cells checked at 24 hours.

| HLA class I cDNA | HSV-2 DNA or peptide | | | | | |
|---|---|---|---|---|---|---|
| | empty vector | pool A1:H3 | clone A1:H3:B8 | ICP0 exon 1 | ICP0 exon 1.2 | ICP0 92–105 |
| empty vector | not done | not done | <2 | <2 | <2 | <2 |
| B*4501 | <2 | 420 | >600 | <2 | >600 | 1,100 |

Figure 5:
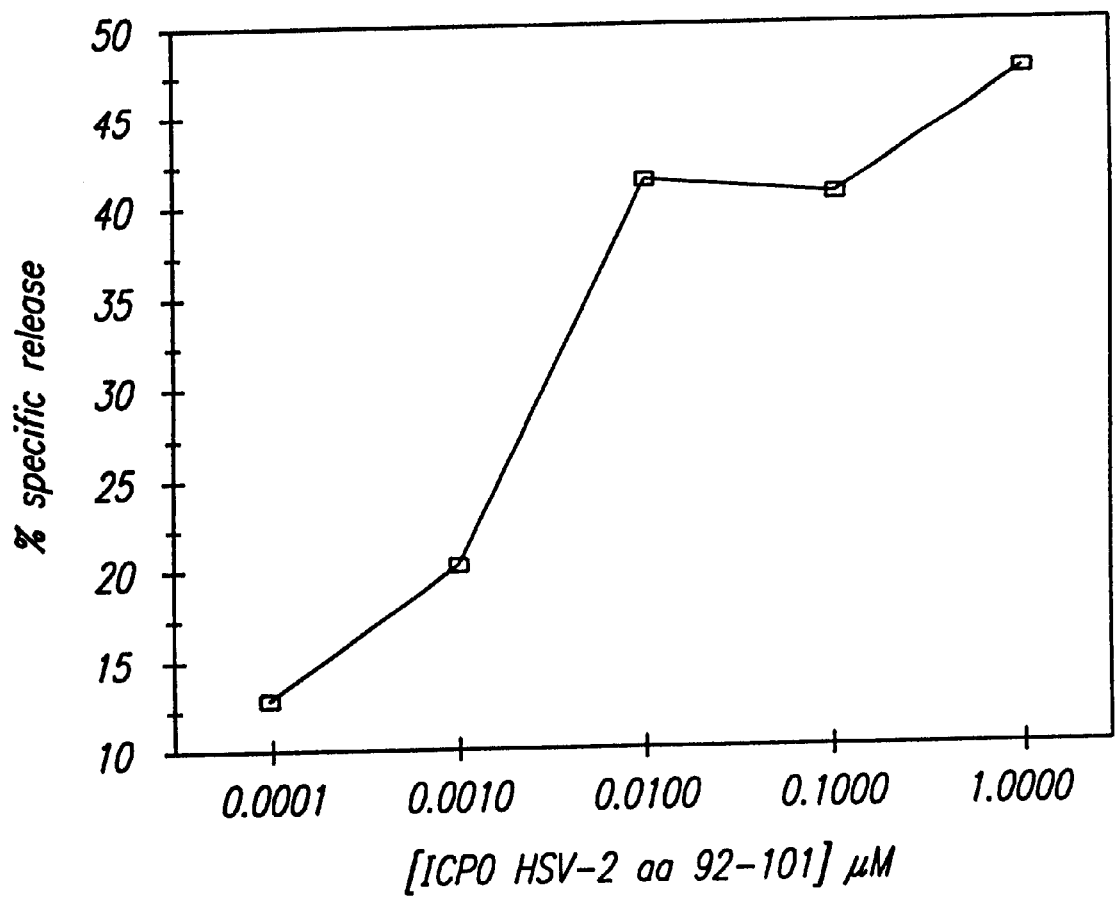
FIG. 5 is a graph showing CTL activity of RW51 against indicated concentrations of synthetic ICP0 92–101. Four-hour $^{51}$Cr release assay with effector:target ratio 10:1. Spontaneous release all <20%.

To choose peptides efficiently, a HLA B45 binding motif was derived from B45-restricted peptides, and pool sequence from peptides eluted from B*4501. The motif is glutamic acid at position 2, hydrophobic at position 10 (P1 and P9 in "binding" nomenclature (Rammansee H-G, Current Opinion in Immunology 1995, 7:85–96)). Peptide ICP0 92–105 (A<u>E</u>RQGSPTP<u>A</u>DAQG; SEQ ID NO: 19) was active in CTL (FIG. 4) and interferon-gamma (Table 4) assays. Other candidate exon 2 peptides were not. The high $EC_{50}$ value (~1 μM) may be due to the carboxy-terminus tail predicted to lie outside the peptide-binding groove and reduce binding to HLA B*4501. Vaccinia-ICP0 from B. Rouse (Manickan E et al., J. Virol. 1995, 69:4711–16) was grown and titered (Koelle D M et al., J. Virol. 1994, 68:2803–10). Clone RW51 specifically lysed vac-ICP0 targets (FIG. 4). The availability of the vaccinia was fortuitous, and not required to confirm the result of expression cloning. To narrow down the epitope, a peptide comprising amino acids 92–101 of ICP0 (AERQGSPTTP; SEQ ID NO: 6) was synthesized. The $IC_{50}$ for this peptide is between 1 and 10 nanomolar (FIG. 5).

To confirm that patients with HSV-2 infection have T-cells reactive with the newly discovered T-cell antigen circulating in their peripheral blood, peripheral blood mononuclear cells (PBMC) from the patient from whom the lesion-derived clone RW51 was recovered were peptide stimulated. PBMC were cultured for three days at $2 \times 10^6$ cells per 1.88 cm² well in 2 ml of T-cell medium containing 1.0 μg/ml peptide HSV-2 ICP0 92–101. On the fourth day, IL-2 (32 units/ml) was added. On the eighth day, the cells were washed and restimulated in the same size well with an additional $2 \times 10^6$ autologous, irradiated (3300 rad gamma irradiation) PBMC, 1.0 μg/ml of the same peptide, and IL-2 (32 U/ml).

Responders were cultured for an additional nine days in the presence of IL-2 and expanded as necessary. Cytotoxicity assay was performed using autologous or HLA class I-mismatched LCL treated either with nothing, peptide HSV-2 ICP0 92–101 at 1 μg/ml for 18 hours, or infection with HSV-2 strain 333 at MOI 10 for 18 hours. The cytotoxicity assay was a standard four-hour $^{51}Cr$ release assay.

Figure 6:
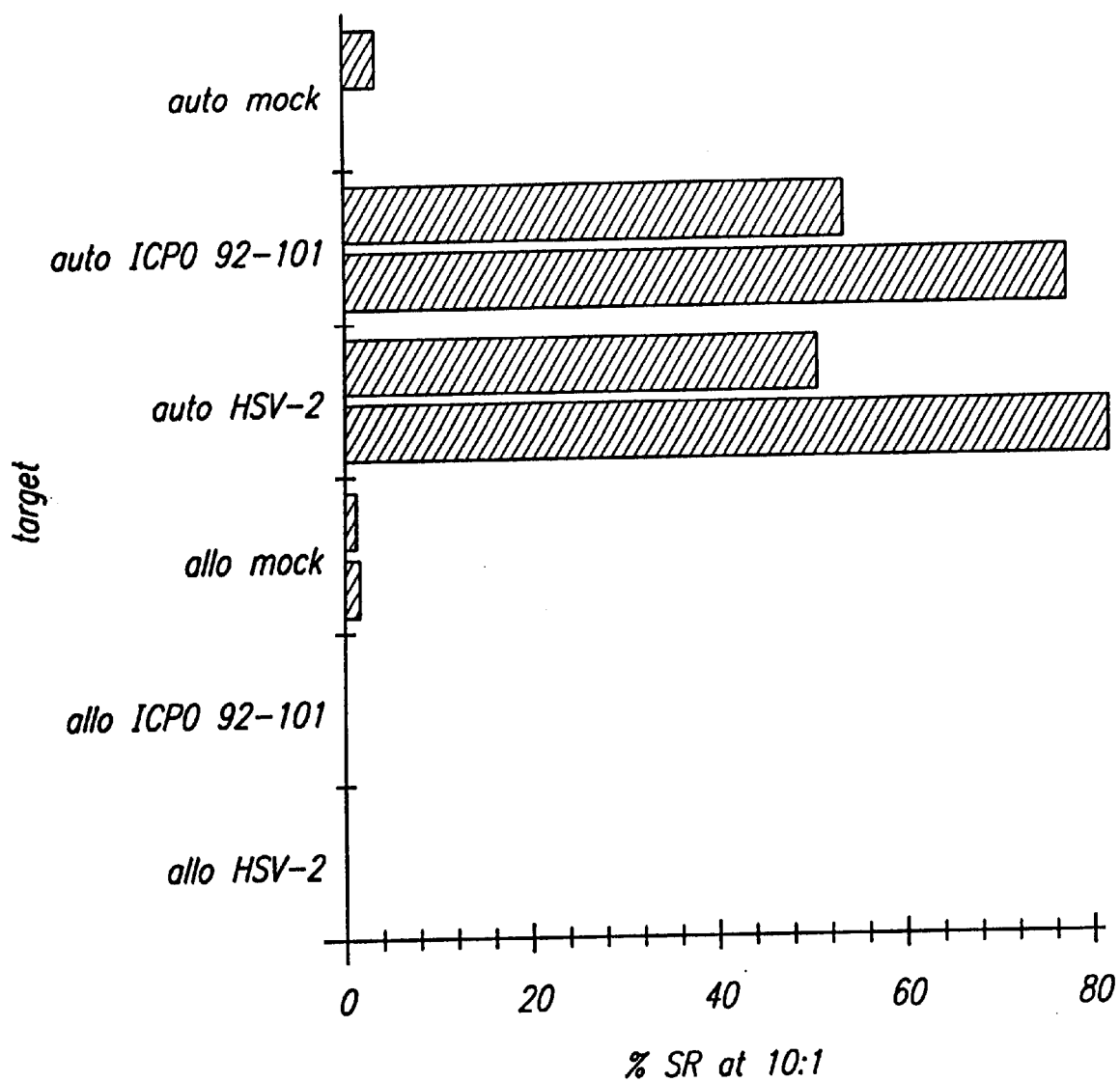
FIG. 6 is a graph showing CTL activity of lymphocytes subject RW, derived from peripheral blood and stimulated with a peptide of HSV-2 ICP0 amino acids 92–101. Four-hour $^{51}$Cr release assay with effector:target ratio of 10:1. Spontaneous release <20%. For each pair of bars, the upper bar represents data from a lesion-derived CD8 clone and the lower bar represents data from PBMC stimulated with peptide.
Figure 7:
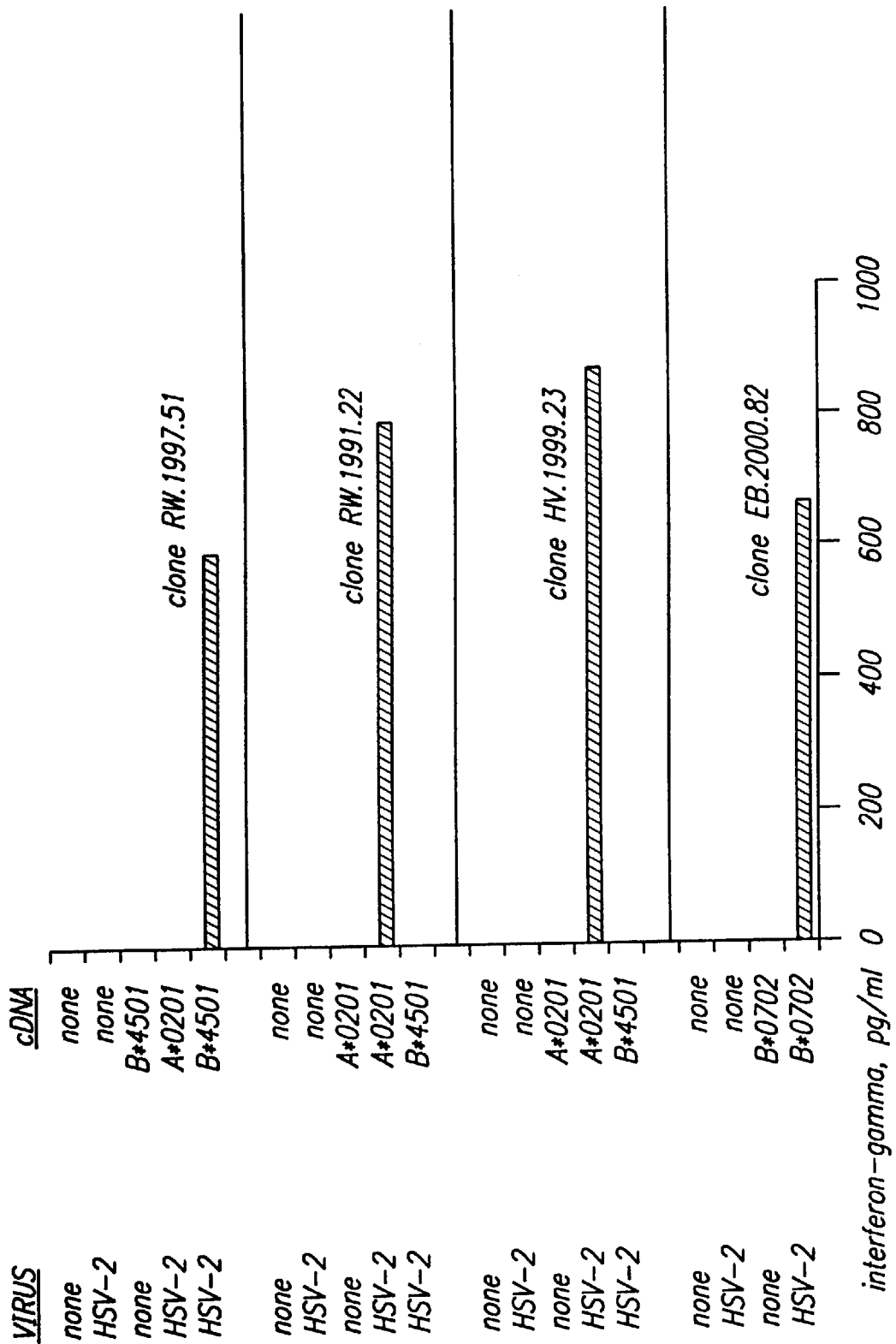
FIG. 7 shows confirmation of HLA restricting allele, HSV-2 reactivity, and IFN-gamma secretion by lesion CD8 clones.
Figure 8A:
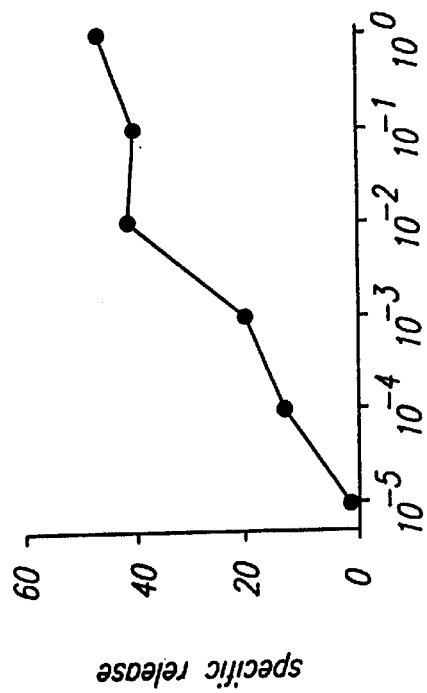
FIG. 8A shows peptide dose-response for lesion CD8 clone dkRW.1991.22 worked up by expression cloning.
Figure 8B:
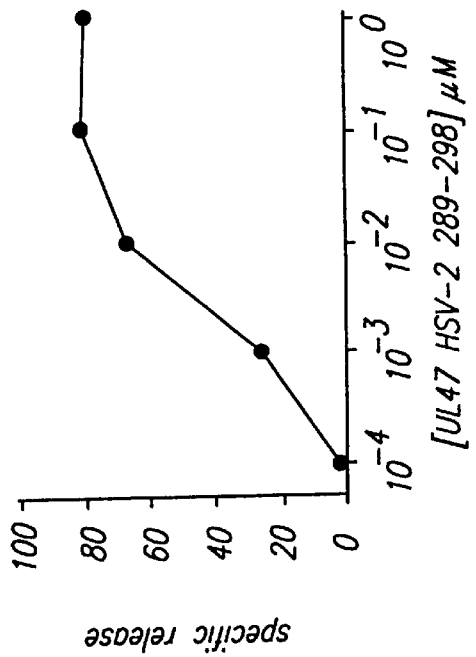
FIG. 8B shows peptide dose-response for lesion CD8 clone RW.1997.51 worked up by expression cloning.
Figure 8C:
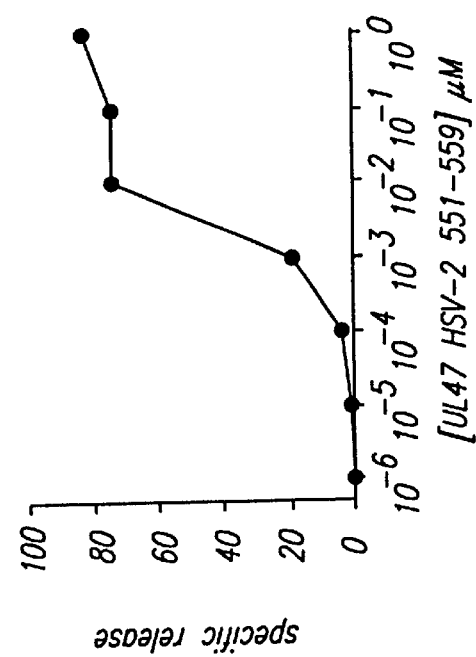
FIG. 8C shows peptide dose-response for lesion CD8 clone HV.1999.23 worked up by expression cloning.
Figure 9:
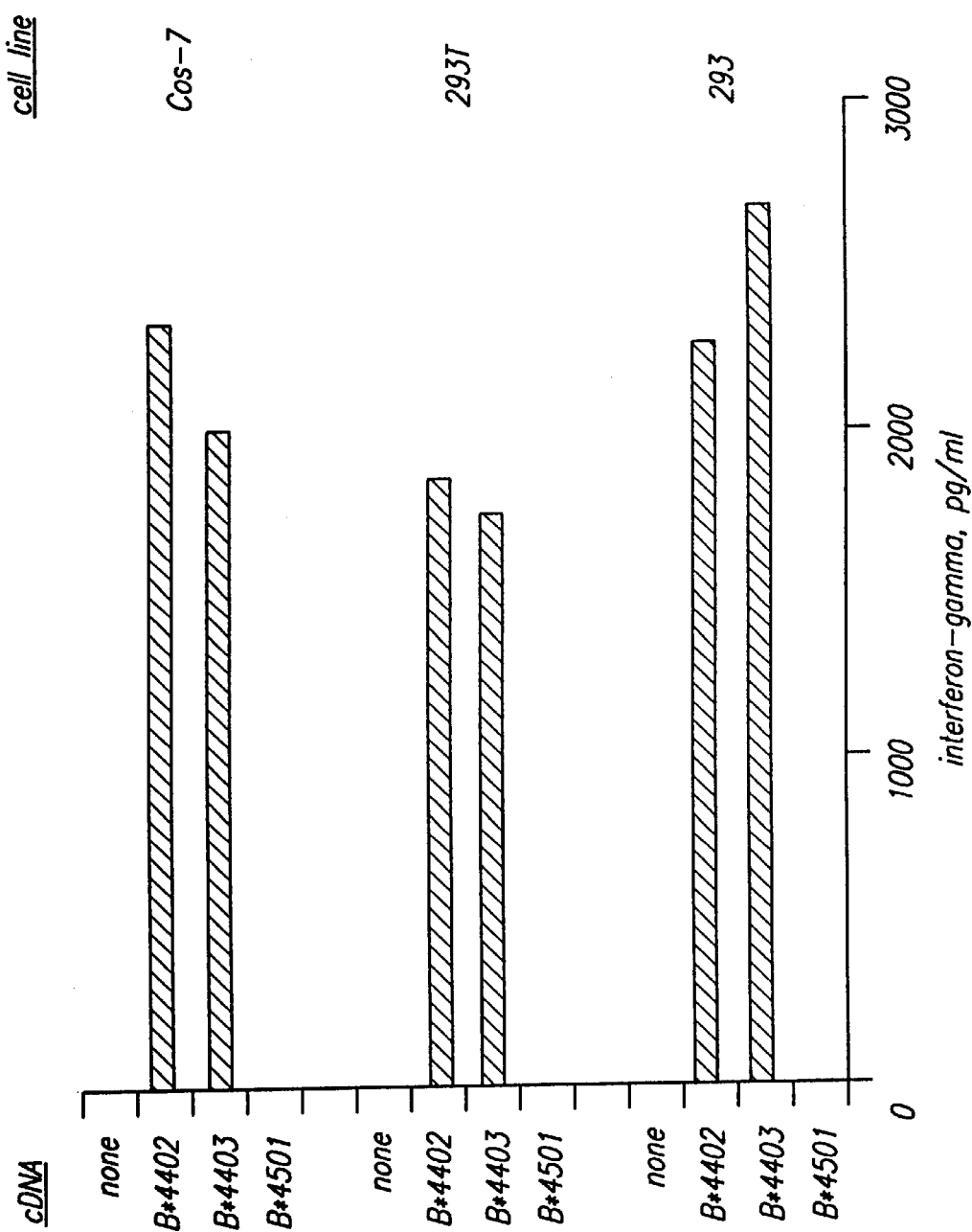
FIG. 9 shows that A*0201 restricted, $U_L47$ 289–298-specific CD8 CTL cross-react with B*4402 or B*4403.

The results (FIG. 6) show that stimulation of PBMC with peptide HSV-2 ICP0 92–101 was able to stimulate cells with cytotoxicity towards HSV-2 infected cells, and that this activity was not present against HLA class I-mismatched cells. For comparison, the index T-cell clone RW51 was also used as an effector cell in this assay and displayed comparable, although slightly higher, cytotoxicity at the effector to target ratio of 10:1 shown in FIG. 6.

Example 5

Identification of an $U_L47$ Antigen Recognized by HSV-specific CD8 CTL

This example demonstrates, via expression cloning, the antigenicity of an HSV polypeptide encoded by DNA contained within the coding region for protein $U_L47$. Expression cloning and library preparation were as described in Example 4.

Lesion clone dkRW22.1991 was chosen for expression cloning. This clone has cytolytic activity against HSV-2 infected, autologous LCL (Table 1). The HLA restricting allele of CD8 TCC dkRW22.1991 is HLA A*0201, as Cos-7 cells transfected with HLA A*0201, but not B*4501, and then infected with HSV-2, specifically stimulated interferon-gamma release from dkRW22.1991 (Table 5). Clone dkRW22.1991 has the following phenotype by flow cytometry: CD3(+), CD4(−), CD8(+), CD16 and 56(−), and T-cell receptor α/β(+).

Results

To screen libraries for the antigenic protein, Cos-7 cells plated (9,000/well) in flat microtiter plates were co-transfected after 24 hours with library pools and A*0201 DNA (50 and 25 ng/well). Cloned T-cells were added 48 hours later, and interferon-gamma assay performed on 24 hour supernatants as described for Example 4. One positive pool in the library from pCNA3.1-his C was found. Bacteria from this pool were plated and DNA made from 96 colonies for the next round of assay. One positive clone, designated C1F1C7, was found in a follow-up round of interferon-gamma release assays. Sequencing of the viral insert revealed that it was a 1.4 kb Sau3a I fragment of the HSV-2 genome from nucleotides 102875 to 101383. The sequences encode the C-terminal region of HSV-2 $U_L47$ from amino acids 292 to 696, a short intervening region, and then the N-terminal 70 amino acids of HSV-2 $U_L46$.

To partially narrow down the region of HSV-2 DNA encoding the antigenic epitope, the full length genes for $U_L47$ and $U_L46$ of HSV-2 were cloned by PCR using a thermostable DNA polymerase with proofreading function (pfu, Invitrogen). The primers were CTA GGATCCCCTCCGGCCACCATGTCC (5' primer; SEQ ID NO: 7) and CGATCTAGACCTATGGGCGTGGCGGGC (3' primer; SEQ ID NO: 8) for $U_L47$, and CGA GGATCCGTCTCCGCCATGCAACGCCG (5' primer; SEQ ID NO: 9) and CGC TCTAGATTTAATGGCTCTGGTGTCG (3' primer; SEQ ID NO: 10) for $U_L46$. In each case, the 5' primer contained an incorporated BamH I site (underlined) and the 3' primer contained an incorporated Xba I site (underlined) to-facilitate cloning.

The PCR products were digested with BamH I and Xba I and cloned into pcDNA3.1-his-C to yield in both cases in-frame fusion proteins. The sequences in the fusion regions at the 5' ends of the HSV-2 genes into pcDNA3.1-his-C were confirmed by sequencing. In addition, all of the $U_L46$ coding sequences contained within the original positive clone C1F1C7 were deleted by restriction digestion and re-ligation. The daughter construct is designated C1F1C7-Apa I(−).

To test the reactivity of lesion-derived T-cell clone, Cos-7 cells were transfected with A*0201 DNA and either infected with HSV-2 or transfected with each of these constructs. The results are consistent with recognition of an antigen encoded by the DNA encoding $U_L47$ of HSV-2. The clone C1F1C7-Apa I(−) was positive. Because this clone is deleted of all $U_L46$ sequences, $U_L46$ is not being recognized. In addition, the transfection of full-length $U_L47$, but not $U_L46$, together with HLA A*0201 into Cos-7 cells yielded cells that specifically stimulated interferon-gamma secretion by clone dkRW22.1991.

TABLE 5

Secretion of interferon-gamma by TCC dkRW22.1991 in response to Cos-7 cells transfected with functional HLA class I heavy chain cDNAs and infected with HSV-2 at multiplicity of infection of approximately 5.

| HLA cDNA | none | A*0201 | A*0201 | B*4501 |
|---|---|---|---|---|
| live HSV-2 | none | none | HSV-2 | HSV-2 |
| IFN-γ, pg/ml | <10 | <10 | >600 | <10 |

TABLE 6

Secretions of interferon-gamma by clone dkRW22.1991 in response to Cos-7 cells transfected with HLA A*0201 and either infected with HSV-2 as a positive control or cotransfected with eukaryotic expression vectors containing specific segments of the HSV-2 genome.

| HLA cDNA | None | A*0201 | A*0201 | A*0201 | A*0201 | A*0201 |
|---|---|---|---|---|---|---|
| Live HSV-2 | None | None | None | None | None | None |
| HSV-2 DNA | None | None | C1F1C7 | C1F1C7 Apa I (−) | $U_L47$ | $U_L46$ |
| IFN-γ, pg/ml | <10 | <10 | >600 | >600 | >600 | <10 |

Example 6

Identification of Amino Acids 289–298 551–559 and 551–561 of $U_L47$ as Antigens Recognized by HSV-specific CD8 CTL Materials & Methods Cell Lines and Viruses:

EBV-LCL were made from PBMC in-house; ARENT, PITOUT, HERLUF, and KAS011 were obtained from G. Nepom. HSV-1 E115 and HSV-2 333 and HG52 and recombinant vac-ICP0-HSV-2 (provided by B. Rouse) and wild type vaccinia NY were raised and tittered in Vero or BSC-40 cells.

HSV-specific T-cells were obtained from HSV-2 culture-positive buttock lesions. Biopsies were taken on lesion day 5 or from herpetic vesicle fluid. Lymphocytes were expanded in bulk with PHA and IL-2. CD8 cells were selected with immunomagnetic beads (Minimacs, Miltenyi) and cloned. For subject HV, biopsy tissue was digested for five hours at 37° C. in Collagenase IV-S (Sigma) and the resultant cell suspension cloned in serial 10-fold dilutions. Clones were expanded with anti-CD3 mAb, IL-2, and feeders. Peptide-restimulated PBMC-derived lymphocytes were made by incubating 4×10⁶ PBMC with 1 μg/ml peptide. After three days, 10 U/ml human recombinant IL-2 (Chiron) was added. After seven days, responders were washed and re-plated with 2×10⁶ freshly thawed, irradiated autologous PBMC, peptide, and IL-2. Cells were assayed on day 14–21.

Expression Cloning:

HSV-2 genomic DNA was digested with Sau3A I, re-extracted, and partially filled in with Klenow fragment, dTTP and dCTP. Plasmids pcDNA3.1 (+) myc-his A, B, and C (Invitrogen) were digested with Xho I and partially filled in with dATP and dGTP. After ligation, DNA was electroporated into E, coli strain DH10B. Each library had several thousand primary transformants. The majority of each library was immediately amplified in bulk (4 ml LB-amp, overnight) and aliquoted. 20 random clones each contained single HSV-2 Sau3A I fragments. To make DNA for transfection, deep 96-well plates were inoculated either with libraries at ~15 colonies/well, or with selected individual clones. After overnight growth, DNA was prepared with 96-well filters.

To make HLA A*0201, B*4402, B*4403, and B*4501 cDNA, total RNA was extracted from LCL. cDNA was prepared with oligo-dT and MMLV reverse transcriptase. PCR used pfu DNA polymerase, 2.5 mM (each) dNTP, cDNA, and primers designed to complement the heavy chain gene and containing distal Kpn I or Xba I sites. Amplimers were digested Kpn I and Xba I and ligated into pcDNA3.0. Insert sequences were identical to Genbank.

To study the cDNA species derived from the positive genomic clone containing portions of ICP0 (below), Cos-7 cells were transfected with the ICP0 genomic clone, and total RNA prepared after 48 hours. The primer used for cDNA synthesis (TGCTCTAGAGACTCGATCCCTGCGCGTCGG, Xba I site underlined; SEQ ID NO: 11) was derived from the sequence of the 3' end of the HSV-2 DNA in the ICP0 genomic clone. MMLV reverse transcriptase was used. To examine splicing, PCR used pfu polymerase, cDNA, the above 3' primer, and 5' primer TAAGGTACCTGAAC-CCCGGCCCGGCACGAGC (Kpn I site; SEQ ID NO: 12). To isolate exon 1 of ICP0, PCR used the same 5' primer and 3' primer TGCTCTAGACCAGGCGTGCGGGGCG-GCGGG (Xba I site; SEQ ID NO: 13). Product was cloned into pCDNA3.1-his-B.

Full-length U$_L$47 of HSV-2 was PCR-cloned into pCDNA3.1-his-C using the same primer identified above (SEQ ID NO: 7, 8). Full-length U$_L$46 of HSV-2 was PCR-cloned into pcDNA3.1-his-C with the corresponding primers identified above (SEQ ID NO: 9, 10). Similarly, constructs expressing amino acids 1–595 and 1–640 of U$_L$47 were made by PCR, using the above 5' primer, appropriate 3' primers, and pCDNA3.1-his-C. Constructs U$_L$47 1–535 and 536–696 were made using a natural Not I site at aa 535. In-frame fusion was confirmed by sequencing.

Lymphocyte Functional Assays:

CTL assays were done by standard 4-hour $^{51}$Cr release. Target EBV-LCL were infected 18 hours with HSV at MOI 10; effector:target ration was 20:1. Anti-class I mAb W6/32 was used at 10 μg/ml. Actinomycin D was used a 5 μg/ml for 30 min. pre-infection, during 90 minute infection, wash, and assay periods to study the effect of inhibition of viral RNA expression.

IFN-gamma secretion by HSV-reactive CD8 CTL was used as the endpoint to confirm isolation of functional HLA cDNA and for expression cloning. Cos-7 cells seeded on day one at 9,000 cells/well in 96-well flat-bottom plates were transfected on day two with 50 ng HLA cDNA (Fugene-6). On day three, cells were infected with HSV-2 333. On day four, 0.7–1.0×10⁵ cloned CD8 T-cells were added. Supernatants were saved on day five.

To screen libraries, Cos-7 were co-transfected with 50 ng HLA cDNA and 100 ng of library DNA (pools of 15, or single colony). Two days later, 1×10⁵ cloned T-cells/well were added and supernatants saved after 24 hours. Positive pools were broken down to identify active bacterial clones. The HSV-2 DNA in active clones was sequenced.

Flow Cytometry:

Lymphocytes were stained with labeled mAb to CD3, CD4, CD8, CD16/56, TCR αβ, or TCR γδ by standard methods. To measure HLA expression in transfected Cos-7 cells, trypsinized cells were mixed with 1 μg FITC-labeled mAb B12 reactive with HLA B*4501 (One Lambda, Inc. or supernatant of mAb MA2.1 cells reactive with HLA A*0201, followed by FITC-labeled goat anti-mouse IgG. HLA typing: For definition of HLA B44 alleles, direct sequencing of variable exons was performed.

ELISA:

Gamma-interferon was measured by ELISA with reagents from Endogen. Plates were coated with 100 μl of 0.25 μg/ml capture mAb M700A-E and blocked with 1% BSA in 0.2. M NaCl, 3mM KCl, 0.05 M Tris, pH 9 (TBS) for one hour. Subsequent incubations were each 100 μl, preceded by 3–5 washes with PBS/0.2% Tween-20, and performed with rotation at room temperature. Samples and standards diluted in TBS with 0.1% BSA, 0.05% Tween-20, and 4 μg/ml Immunoglobulin Inhibiting Reagent #6LD1068 (Bioreclamation, Inc., East Meadow, N.Y.) (sample buffer) were added for 2 hours. Biotinylated detection mAb (M701B) diluted to 100 ng/ml in sample buffer was added for one hour. AvidinD:HRP (A-2004) diluted to 100 ng/ml in TBS with 1% BSA, 0.05% Tween-20 was added for one hour. TMB substrate was added for 10 minutes. Lower limit of detection ranged from 2 to 10 pg/ml.

Results are shown in FIGS. 7–10 and in Tables 7–9.

TABLE 7

| | autologous | | | | HLA mismatched[1] | | partially HLA matched[2] | |
|---|---|---|---|---|---|---|---|---|
| T-cell clone | mock | HSV-1 | HSV-2 | HSV-2/ Act D[3] | mock | HSV-2 | allele | mock | HSV-2 |
| dkRW.1997.51 | 1 | 3.7 | 73.6 | 45.1 | 2.9 | 4.5 | B*4501 | 0 | 61.8 |
| dkRW.1991.22 | 1.2 | 0.1 | 38.3 | 12.1 | 0 | 0 | A*0201 | 3.3 | 65.2 |
| HV.1999.23 | 6 | 0 | 56.6 | 35.8 | 2.5 | 2.1 | A*0201 | 0 | 33.4 |

TABLE 8

| T-cell clone | HLA cDNA | genomic clone | HSV-2 sequence (nucleotides) | HSV-2 ORF(s) amino acids |
|---|---|---|---|---|
| dkRW.1997.51 | B*4501 | A1:H3:B8 | 1,858–3,022 | ICP0 1–105 |
| dkRW.1991.22 | A*0201 | C1:F1:C7 | 102,875–101,383 | UL47 299–696 . . . UL46 1–71 |
| HV.1999.23 | A*0201 | C2:C10:B9 | 102,943–102,875 | UL47 278–298 |

TABLE 9

| | HLA class I alleles | | Lysis | |
|---|---|---|---|---|
| EBV-LCL | HLA A | HLA B | uninfected | HSV-2-infected |
| autologous | *01, *0201 | *08, *57 | 9.1 | 70.4 |
| CW 7477 | *0301, *11 | *4402, 1801 | 70.3 | 94.2 |
| HERLUFF | *02 | *4402, 35 | 60.0 | nd$^2$ |
| HH 7894 | *03, *31 | *4402, *1524 | 77.2 | 75.5 |
| KK 6806 | *02, *03 | *4402, *2705 | 57.4 | 62.3 |
| PITOUT | *2902 | *4403 | 71.0 | 51.2 |
| MK 8080 | *03, *30 | *4405, *39 | 2.6 | 1.0 |

The results show that lesion-infiltrating CD8 CTL recognize immediate early (ICP0) or virion input ($U_L47$) proteins as predicted by ACT D inhibition and HSV-encoded TAP and transcriptional inhibitors. Moreover, HSV-2 $U_L47$ 289–298/A*0201-specific CD8 CTL cross-react with HLA B*4402 and B*4403, but not B*4405. The TCR may recognize these B44 alleles plus a "housekeeping" peptide, currently unknown, present within B cells and also human and primate renal epithelial cells. The data suggest that cross reactive T-cells could mediate GVHD when stem cells from a A*0201/not B*4402 or *4403 person are placed into a A*0201, HSV-2 infected person as well as graft rejection when a B*4402 or *4403-bearing organ is placed into a A*0201, HSV-2 infected person.

Example 7

Identification of Amino Acids 548–557 of $U_L47$ as Antigens Recognized by HSV-specific CD8 CTL CD8+ T cell clone cpRW22 (separately derived from same source as dkRW22) was tested against a series of synthetic peptides predicted to bind to HLA-A2 and derived from the HSV-2 gene $U_L47$. One of these peptides was positively recognized by cpRW22 in an IFNγ ELISPOT assay. The sequence of the $U_L47$ peptide that scored positive was: NH2-RLLGLADTVV-COOH (SEQ ID NO: 18), which peptide contains amino acids 548–557 of $U_L47$.

A series of 10-mer ($U_L47/549$–558, 550–559, 551–560 and 552–561) and 9-mer peptides ($U_L47/548$–556, 549–557, 550–558, 551–559 and 552–560) that overlapped $U_L47/548$–557 was prepared to better define the optimal target peptide. One 9-mer ($U_L47/551$–559) and two 10-mer ($U_L47/550$–559, 551–560) scored strongly positive at low concentrations in an ELISPOT assay (FIGS. 11A & 11B). The $U_L47/550$–559 and $U_L47/551$–559 peptides had similar activities at all peptide concentrations tested.

Example 8

Identification of Amino Acids 550–559 of $U_L47$ as a Naturally Processed Antigen To determine the naturally processed $U_L47$ peptide, A2-molecules were purified from $1.5 \times 10^{10}$ C1R-A2/3D9.6H7 cells and the bound peptides stripped by acid elution. These peptides were fractionated on an HPLC column under the following conditions: TFA ion-pairing agent; 0–10% acetonitrile (ACN) over 5 mins, 10–45% ACN over 50 mins, 45–60% ACN over 5 mins. These fractions were tested for the ability to sensitize T2 targets for recognition by, cpRW22 T cells in an IFN-gamma ELISPOT assay. Targets were T2 cells (20,000) pulsed with 5% of each fraction in serum-free medium+3 μg/ml HuB2M at 32° C. for 4 hours. The targets were then washed twice and transferred to duplicate wells (10,000/well) of ELISPOT plates. Responders were CTL clone cpRW22 (20,000/well).

Fractions 17, 18 and 23 were found to contain this activity (FIG. 12). Fractions 17 and 18 were subfractionated on the HPLC column under the following conditions: HFBA ion-pairing agent; 0–10% ACN over 5 mins, 10–35% ACN over 50 min, 35–60% ACN over 5 mins. Subfractions 24 and 25 were found to sensitize T2 cells for recognition by cpRW22 (FIG. 13B; compare FIGS. 13A & 13C). Fraction 23 was subfractionated by HPLC in the same manner. Subfraction 37 was found to sensitize T2 cells for recognition by cpRW22 in an IFN-gamma ELISPOT assay (FIG. 14). The $U_L47/551$–559, 550–559, and 551–560 peptides were run on the HPLC under the subfractionation conditions and found to elute in fractions 37 ($U_L47/550$–559; FIG. 15A), 40/41 ($U_L47/551$–560; FIG. 15B), and 32 ($U_L47/551$–599; FIG. 15C).

The $U_L47/550$–559 elutes in the same fraction (37) as does the naturally processed peptide from C1R-A2/3D9.6H7 cells, and is therefore likely to have the same sequence as the naturally processed peptide. The MS/MS data for Fraction 23/Subfraction 37 shows the presence of a peptide with a molecular mass of 961 (FIG. 16). The molecular mass of $U_L47/550$–559 is also 961. This provides supportive evidence that $U_L47/550$–559 is the naturally processed $U_L47$ peptide.

The amino acid sequence of the $U_L47/550$–559 peptide is LGLADTVVAC (SEQ ID NO: 1). It was subsequently verified that a gene fragment of HSV-2 that could encode the $U_L47/550$–559 peptide is contained within C1R-A2/3D9.6H7 cells. This was done by performing PCR with primers made to flanking regions of the cloning site of the pBIB retroviral vector and to the DNA sequence encoding $U_L47/550$–559 (FIG. 17). Using these PCR primers and varying the PCR conditions, it was demonstrated that the C1RA2/3D9.6H7 cells contain at least two retroviral inserts derived from HSV-2 (FIGS. 18A–C). One insert encodes two fragments of the $U_L52$ gene. The second insert encodes a large portion of the $U_L47$ gene, including the portion encoding the $U_L47/550$–559 peptide.

Example 9

Methods for Identifying Proteins Recognized by HSV-specific CD8 CTL

This example demonstrates how one can identify additional proteins recognized by HSV-specific CD8 CTL using lesion-derived material.

Isolation of HSV-specific CD8 T-cells from Genital/bullock HSV-2 Lesions

Punch biopsies (3–4 mm) are taken from perirectal, buttock and/or thigh skin after cleansing and anesthesia. Lesions from suspected primary herpes are biopsied as soon as possible, and serial biopsies at least twice during primary infection are preferred. Recurrent genital HSV-2 lesions in healing stages (late ulcer/crust) are preferred for antigen/epitope discovery as LIL from such lesions have high CTL activity. Portions of lesions can be snap frozen in isopentane/liquid nitrogen in OCT media for immunohistology. A portion of the biopsy is dissociated and cells grown in limiting dilution, and a portion used for bulk culture (Koelle D M et al., J. Clin. Invest. 1998,101:1500–1508). LIL are expanded in bulk by mincing tissue and stimulating with 0.8 μg/ml PHA and $7.5 \times 10^5$ feeders PBMC/well in 48-well plates in T-cell medium with acyclovir (50 μM). Expansion is assisted by IL-2 (50 U/ml, Hemagen) and usually yields $1–5 \times 10^7$ cells in 14–21 days. CTL activity of CD8-selected cells is tested against autologous and allogeneic mock- and HSV-2 infected LCL in 4-hour $^{5o}$Cr release assays at effector:target 20:1 (Tigges M A et al., J. Virol. 1992, 66:1622–34). Lytic activity at this stage is predictive of recovery of HSV-specific CD8 CTL clones.

To increase the recovery of rare CD8 CTL or CTL that might have a growth disadvantage in bulk culture, one can bypass the initial bulk expansion step. HSV-2 lesions are vesicular during the mid-phase of lesion evolution. HSV-specific CD8 CTL can be cloned from vesicle fluid as follows. Vesicles are broken and fluid recovered with cell scrapers into medium. A portion is used for cytospin preps (preserved at −70° C. after fixation). After Ficoll underlay and standard density gradient centrifugation, cells at the interface are washed and plated in serial dilutions from 100 to 1 cell/well in 96-well U bottom plates together with cloning cocktail (below). The cell recovery from vesicles is typically about $1 \times 10^4 – 2 \times 10^5$ per lesion.

T-cell cloning uses established procedures (Koelle D M et al., J. Infect. Dis. 1994, 169:956–61). CD8-selected cells from a round of bulk expansion of LIL are seeded at 2 and 0.3 cells/well. Cells from freshly disrupted lesion biopsies or vesicle fluid are plated in a modified limiting dilution scheme starting at 30–100 cells/well and decreasing at 2–3 fold steps down to 1 cell/well as reported in Koelle et al., 1994, supra. For CD8-enriched fresh LIL and vesicle cells, a portion can be expanded in bulk (Koelle D M et al., J. Clin. Invest. 1998, 101:1500–1508). Microcultures are fed twice weekly with IL-2 and screened at ~14 days. The percent of wells showing growth at each input number is recorded to estimate the probability of clonality of microcultures.

Screening Candidate Cultures

A preferred screen for candidate cultures is a split-well CTL assay against autologous LCL infected (18 hours, MOI 10) by HSV-2 or uninfected. LCL are EBV-transformed B-cell lines (Koelle D M et al., J. Clin. Invest. 1993, 91:961–68; Miller G et al., Proc. Natl. Acad. Sci. USA 1972, 69:383–87) that take about six weeks to establish from PBMC. LCL are permissive for HSV infection, but are relatively resistant to HSV-mediated HLA class I downregulation in comparison to dermal fibroblasts. Most subjects are enrolled and LCL made prior to biopsy. LCL will therefore be available when TCC are ready for screening. Preferably, the autologous HSV-2 are isolated, grown and titered on Vero cells (Koelle et al., 1993, supra).

For clones derived from bulk-expanded LIL, the cell input number yielding 37% or less of wells positive for growth are designated as probable "clones". Half of each microculture is plated in duplicate (final, ⅛ of the culture/assay well) with $2 \times 10^3$ targets for an effector:target ratio of ~15:1. Clones with a net lysis of HSV-2-infected targets of 15% above their lysis of uninfected targets are considered positive. Clones with CTL activity are analyzed by flow cytometry, and CD8-bearing CTL clones are expanded. Microcultures from fresh, disrupted lesion biopsies and vesicles will have been expanded in a limiting dilution format (above). Without the prior round of bulk expansion, there will be less of a chance that microcultures will contain "sister" clones, although it is possible that identical cells may be independently recovered from the fresh lesion material in separate microcultures.

Expanding Cultures with CTL Activity

T-cells scoring positive in screening assays are expanded by the method of Riddell et al. (Nature Medicine 1996, 2:216–23; U.S. Pat. No. 5,827,642). The "leftover" half of cells in an original microculture well (~$5 \times 10^4$ cells) is mixed in 25 ml T-cell medium (Koelle DM et al., J. Infect. Dis. 1994, 169:956–61) with $2.5 \times 10^7$ irradiated (3300 rad) mixed allogeneic PBMC, $5 \times 10^6$ irradiated (8000 rad) LCL, and 30 ng/ml mAb OKT3 (anti-CD3). At 24 hours and then twice weekly, rhIL-2 (50 U/ml, Chiron, Emeryville, Calif.) is added. OKT3 is removed by washing on day four. Typically, the T-cells expand to $1–5 \times 10^7$ cells at the end of the first cycle. A confirmatory CTL assay can be done when growth visibly slows at about 12 days. The cell number stored after an identical second cycle is essentially unlimited, as a further 200–1000 fold expansion usually occurs. Thawed aliquots of expanded cells work in CTL, proliferation, and cytokine assays. About 10–20% of clones fail to expand; loss of antigenic specificity is rare, but loss of replicative potential may occur.

The Cos-7 co-transfection method described above can be used for expression cloning. DNA from the sequenced HSV-2 strain HG52 can be used, digested with Sau3A I and ligated into each member of the pcDNA3.1 (+) his series. The cDNA encoding the HLA class I heavy chains restricting the TCCs selected for expression cloning can be cloned, if necessary, by RT-PCR into pcDNA3.0 as described above. A universal method has been published (Ennis PD et al., Proc. Natl. Acad. Sci. USA 1990, 87:2833–37). Proof-reading polymerase can be used and cDNAs sequenced. Primers are allele-specific perfect matches with "tails" containing endonuclease sites not present in the target sequence. Undesired heavy chain PCR product (which may be co-amplified) can be reduced by digestion of PCR product with an enzyme that preferentially cuts the undesired cDNA. To test cDNA function, it can be 1) checked for cell surface expression in 48 hour-transfected Cos-7 cells with allele-specific mAb, and 2) checked for presentation of HSV-2 antigen presentation by the method illustrated in Table 3 above. The expected results are specific staining of Cos-7 cells with allele-specific mAb after transfection of heavy chain; empty vector and control mAb are included. Specific stimulation of CD8 TCC interferon-gamma secretion by Cos-7 cells transfected with the heavy chain and infected with HSV-2 is expected.

The number of clones screened per library will depend on the number of restriction fragments generated in making the library, but will typically be several thousand. Pool size (number of clones transfected per well of Cos-7 cells) will start at ~15 viral DNA fragments/well. Positive pools are broken down and individual clones tested. Positive clones are sequenced and compared to the published HSV-2 sequence to identify antigens.

Epitope Mapping

Epitope mapping can be done with molecular, bioinformatic, and synthetic methods. Genomic library screening (above) yields gene fragments as initial "positives" that range from 25 to 300 amino acids long. The HSV-2 coding sequences in positive molecular clones can be shortened using standard methods, such as exonuclease III digestion (Gavin MA et al., J. Immunol. 1993, 151:3971–89) to make nested truncations of the HSV-2 insert or cleavage of HSV-2 DNA at internal restriction sites and reconstruction of plasmids. It is preferable to use PCR with a proofreading polymerase to re-amplify a portion of the positive construct. Truncations are designed for a 50–100 amino acid-long positive fragment. For motif-matching peptides, the P1 "anchor" is placed at residue 2 of synthetic peptides, since the N-terminal peptide at position "P minus 1" frequently faces "up" to the TCR and is required for T-cell triggering. If no motif is known, 15-mer peptides overlapping by five are made. Peptides are tested at 1 and 10 μM in CTL and/or interferon-gamma assays.

If these methods do not find the epitope, further molecular "trimming" from both ends of the active HSV-2 construct can be done to find the minimal coding sequence (Schneider J et al., Int. J. Cancer 1998, 75:451–58). If this peptide still is not positive in CTL assay, it may be that post-translational modification is required. The peptide predicted to be positive by molecular genetic methods is loaded into the APC by electroporation or osmotic shock (Chen W et al., J. Immunol. Methods 1993, 15:49–57).

Example 10

ICP0 Stimulation of CTL Responses in Additional HLA-B45 Subjects

This example demonstrates that other HLA-B45 positive donors have detectable CD8+ T cell responses to the previously defined ICP0 92–101 peptide.

Peptide restimulation in bulk format are appropriate for sensitive detection of CTL, while lesion derived antigen (LDA) formats yield CTL levels, but require prolonged cell replication for detection. In this example, $4\times10^6$ PBMC in 2 ml T-cell medium were stimulated with 1 μg/ml HSV-2 peptides, and IL-2 (10–30 U/ml) was added on day 3. On day 8, responders were washed and restimulated in 2 ml with $2\times10^6$ autologous irradiated PBMC, fresh peptide, and IL-2, and split as necessary until assay on day 14–16. For two HLA B*4501-bearing persons including the index subject, convincing HLA class-restricted CD8 CTL were detected that not only lysed peptide-loaded targets, but also killed HSV-2-infected targets and were inhibited by anti-class I mAb (Table 10).

TABLE 10

Lysis of HLA B*4501 LCL by PBMC stimulated with peptide HSV-2 ICP0 92-101, or (+) control clone RW.1997.51. Results are percent specific release in four-hour CTL assays at effector to target ratio of 10:1–20:1.

| | target[1] | | | | | | |
|---|---|---|---|---|---|---|---|
| effector | RW mock | RW peptide[1] | RW HSV-2 | RW HSV-2/ anti-class I[2] | HV mock | HV peptide | HV HSV-2 |
| RW PBMC | 1 | 45.3 | 48.2 | 12.2 | 0 | −1 | 0 |
| PO PBMC | 0 | 54.9 | 33.5 | 5.8 | 4 | −1 | 0 |
| clone RW.1997.51 | 0 | 65.3 | 67.3 | 5.2 | 1 | 0 | 2 |

[1]Target LCL (RW = B*4501, HV = not B*4501) loaded with 1 μg/ml IGP0 92–101 for 90 minutes, or HSV-2 infection, MOI 5,18 hours.
[2]Anti-HLA class I mAb W6/32 included at 10 μg/ml.

Example 11

$U_L$47 stimulation of CTL Responses in Additional HLA-A2 Subjects

This example demonstrates that other HLA-A2 positive donors have detectable CD8+ T cell responses to the previously defined $U_L$47 peptide 550–559.

The $U_L$47 gene was amplified by PCR methods from genomic HSV-2 (strain 333) DNA and cloned into the pBIB retroviral vector. DNA was prepared from several $U_L$47/pBIB clones and transfected into VA13 cells that stably express HLA-A2. These transfectants were recognized by the $U_L$47/550–559-specific, HLA-A2-restricted CTL clone cpRW22 (FIG. 19). $U_L$47/550–559 peptide-pulsed VA13/A2 cells were used as a positive control.

PBMC from several HLA-A2 positive donors (RW1874, HV5101, AD116, AD120 and AD124), some of whom were seropositive for HSV-2, were tested for the presence of $U_L$47-specific CD8+ T cells. The $U_L$47/550–559-specific, HLA-A*0201-restricted CTL clone cpRW22 was previously derived from donor RW1874. The HSV-2 $U_L$47/289–298 (FLVDAIVRVA; SEQ ID NO: 20)-specific, A2-restricted clone HV2 was derived from donor HV5101. Thus, detection of $U_L$47-specific CD8+ T cells in the PBMC of RW1874 and HV5101 was expected. PBMC were stimulated twice in vitro with 1 pg/ml of one of three A2-restricted epitopes: influenza M1/58–66, $U_L$47/289–298 or $U_L$47/550–559. The T cells were then tested in a $^{51}$Cr-release assay against targets pulsed with either no peptide, the stimulating peptide, or a control peptide (RT) derived from HIV. All of the donors tested are known to be HIV negative.

Results are shown in FIGS. 20A–L. RW1874 responded only to the M1 and $U_L$47/550–559 peptides (FIGS. 20A–C). HV5101 responded to all three peptides (FIGS. 20D–F), even though $U_L$47/289–298 is the only HSV-2 peptide that was identified using cells from this donor. AD120 did not respond to any of the three peptides (FIGS. 20G–I), suggesting that it may belong to a significantly distinct A2 subtype. AD124 responded to the M1, but not to either of the U$_L$47 peptides (FIG. 20J–L). This was expected because AD124 is seronegative for HSV. These results are summarized in Table 11.

TABLE 11

Summary of CD8+ T cell responses to UL47 epitopes.

| Donor | HLA-A2 | Serostatus | | CTL response (PBMC) | | | |
|---|---|---|---|---|---|---|---|
| | | HSV-1 | HSV-2 | M1 | UL47/550 | UL47/289 | RT |
| RW1874 | + | | + | + | + | − | − |
| HV5101 | + | | + | + | + | + | − |
| AD116 | + | − | + | + | − | − | − |

TABLE 11-continued

Summary of CD8+ T cell responses to UL47 epitopes.

| Donor | HLA-A2 | Serostatus | | CTL response (PBMC) | | | |
|---|---|---|---|---|---|---|---|
| | | HSV-1 | HSV-2 | M1 | UL47/550 | UL47/289 | RT |
| AD120 | + | + | + | − | − | − | − |
| AD124 | + | − | − | + | − | − | − |

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A pharmaceutical composition comprising a herpes simplex virus (HSV) polypeptide, wherein the polypeptide comprises amino acids 289–298 (SEQ ID NO: 20), 548–557 (SEQ ID NO: 18), 550–559 (SEQ ID NO: 1), 551–559 (SEQ ID NO: 3), 551–560 (SEQ ID NO: 2) or 551–561 (SEQ ID NO: 21) of $U_L$47 and a pharmaceutically acceptable carrier.

2. The pharmaceutical composition of claim 1, wherein the polypeptide is a fusion protein.

3. The pharmaceutical composition of claim 2, wherein the fusion protein is soluble.

4. The pharmaceutical composition of claim 1, further comprising an adjuvant.

5. The pharmaceutical composition of claim 1, wherein the HSV is HSV-2.

6. A pharmaceutical composition comprising a polynucleotide that encodes amino acids 289–298 (SEQ ID NO: 20), 548–557 (SEQ ID NO: 18), 550–559 (SEQ ID NO: 1), 551–559 (SEQ ID NO: 3), 551–560 (SEQ ID NO: 2) or 551–561 (SEQ ID NO: 21) of $U_L$47, and a pharmaceutically acceptable carrier.

7. The pharmaceutical composition of claim 6, further comprising an adjuvant.

8. The pharmaceutical composition of claim 6, wherein the HSV is HSV-2.

9. A method of inducing an immune response to an HSV infection in a subject comprising administering the composition of claim 1 to the subject.

10. A method of inducing an immune response to an HSV infection in a subject comprising administering the composition of claim 6 to the subject.

11. A method of treating an HSV infection in a subject comprising administering the composition of claim 1 the subject.

12. A method of treating an HSV infection in a subject comprising administering the composition of claim 6 to the subject.

* * * * *

UNITED STATES PATENT AND TRADEMARK OFFICE
CERTIFICATE OF CORRECTION

PATENT NO. : 6,413,518 B1
DATED : July 2, 2002
INVENTOR(S) : David M. Koelle et al.

It is certified that error appears in the above-identified patent and that said Letters Patent is hereby corrected as shown below:

Column 48,
Line 39, after "1", insert -- to --.

Signed and Sealed this

Twenty-ninth Day of July, 2003

JAMES E. ROGAN
*Director of the United States Patent and Trademark Office*